US012778532B2

(12) United States Patent
Cai et al.

(10) Patent No.: US 12,778,532 B2
(45) Date of Patent: Nov. 3, 2026

(54) METHODS FOR QUANTIFYING PANCREATIC BETA CELL FUNCTION AND MASS PROPERTIES WITH RADIOMANGANESE POSITRON EMISSION TOMOGRAPHY

(71) Applicant: Wisconsin Alumni Research Foundation, Madison, WI (US)

(72) Inventors: Weibo Cai, Madison, WI (US); Robert Nickles, Madison, WI (US); Reinier Hernandez, Madison, WI (US); Stephen Graves, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 360 days.

(21) Appl. No.: 15/928,812

(22) Filed: Mar. 22, 2018

(65) Prior Publication Data

US 2018/0271470 A1 Sep. 27, 2018

Related U.S. Application Data

(60) Provisional application No. 62/475,571, filed on Mar. 23, 2017.

(51) Int. Cl.
*A61B 6/00* (2024.01)
*A61B 5/00* (2006.01)
(Continued)

(52) U.S. Cl.
CPC ........... *A61B 6/5217* (2013.01); *A61B 5/425* (2013.01); *A61B 6/037* (2013.01); *A61B 6/4057* (2013.01);
(Continued)

(58) Field of Classification Search
CPC ..... A61B 6/5217; A61B 6/037; A61B 6/4057; A61B 5/425; A61K 51/121; A61K 51/00;
(Continued)

(56) References Cited

U.S. PATENT DOCUMENTS

2010/0196274 A1* 8/2010 Ichise .................... A61K 51/00 424/1.81
2011/0228999 A1* 9/2011 Hsieh .................... G06T 11/006 382/131
(Continued)

OTHER PUBLICATIONS

Dhyani AH, Fan X, Leoni L, Haque M, Roman BB. Empirical mathematical model for dynamic manganese-enhanced MRI of the murine pancreas for assessment of beta-cell function. Magn Reson Imaging. 2013; 31:508-14. (Year: 2013).*
(Continued)

*Primary Examiner* — Christopher Koharski
*Assistant Examiner* — Farouk A Bruce
(74) *Attorney, Agent, or Firm* — Quarles & Brady LLP

(57) ABSTRACT

Methods for imaging beta cells in pancreatic tissue using radioisotopes of manganese, which may be referred to as radiomanganese, are described. Example radioisotopes of manganese include Mn-52g, Mn-52m, and Mn-51. As one example, radiomanganese can be used to image pancreatic beta cells, in which radiomanganese shows a preferential uptake. This provides for applications such as quantifying beta cell mass (e.g., functional beta cell mass), assessing transplant viability, and monitoring the efficacy of drug treatments. A pharmacological agent can be administered to modulate the uptake of divalent metals by the pancreatic beta cells, which can be correlated to a modulated uptake of radiomanganese to estimate pancreatic beta cell mass, function, or both.

25 Claims, 11 Drawing Sheets
(8 of 11 Drawing Sheet(s) Filed in Color)

(51) Int. Cl.

| | |
|---|---|
| ***A61B 6/03*** | (2006.01) |
| ***A61B 6/40*** | (2024.01) |
| ***A61K 31/18*** | (2006.01) |
| ***A61K 31/4422*** | (2006.01) |
| ***A61K 51/00*** | (2006.01) |
| ***A61K 51/12*** | (2006.01) |
| ***G01R 33/48*** | (2006.01) |
| ***G06T 7/00*** | (2017.01) |

(52) U.S. Cl.
CPC .......... *A61K 31/18* (2013.01); *A61K 31/4422* (2013.01); *A61K 51/00* (2013.01); *A61K 51/121* (2013.01); *G06T 7/0014* (2013.01); *G01R 33/481* (2013.01); *G06T 2207/10104* (2013.01); *G06T 2207/30092* (2013.01)

(58) Field of Classification Search
CPC .. A61K 31/4422; A61K 31/18; G06T 7/0014; G06T 2207/10104; G06T 2207/30092; G01R 33/481; G16H 50/30
See application file for complete search history.

(56) References Cited

U.S. PATENT DOCUMENTS

| | | | | |
|---|---|---|---|---|
| 2014/0056812 A1* | 2/2014 | Weissleder | A61K 51/08 530/308 |
| 2014/0105823 A1* | 4/2014 | Muller | C07K 14/4713 435/7.1 |
| 2017/0119330 A1* | 5/2017 | Tichauer | A61B 5/055 |

OTHER PUBLICATIONS

Poole DS, Doorenweerd N, Plomp JJ, Mahfouz A, Reinders MJ, van der Weerd L. Continuous infusion of manganese improves contrast and reduces side effects in manganese-enhanced magnetic resonance imaging studies. Neuroimage, 147 (2017), pp. 1-9. (Year: 2017).*

Eriksson O, Selvaraju R, Eich T, Willny M, Brismar TB, Carlbom L, Ahlstrom H, Tufvesson G, Lundgren T, Korsgren O. Positron emission tomography to assess the outcome of intraportal islet transplantation. Diabetes. 2016; 65:2482-2489. (Year: 2016).*

Bhartiya D. Stem cells to replace or regenerate the diabetic pancreas: Huge potential & existing hurdles. Indian J. Med. Res. 2016; 143:267-74. doi: 10.4103/0971-5916.182615. (Year: 2016).*

Eriksson, Olof. (2011). Imaging Islets of Langerhans by Positron Emission Tomography: Quantification of Beta-Cell Mass in the Native Pancreas and the Islet Graft. Acta Universitatis Upsaliensis. Digital Compreshensive Summaries of Uppsala Dissertations from the Faculty of Medicine 635. 67 pp. Uppsala. (Year: 2011).*

Graves SA, Hernandez R, Fonslet J, England CG, Valdovinos HF, Ellison PA, Barnhart TE, Elema DR, Theuer CP, Cai W, Nickles RJ, Severin GW. Novel Preparation Methods of (52)Mn for ImmunoPET Imaging. Bioconjug Chem. Oct. 21, 2015;26(10):2118-24. doi: 10.1021/acs.bioconjchem.5b00414. Epub Sep. 10, 2015. (Year: 2015).*

Topping GJ, Schaffer P, HoehrC, Ruth TJ, Sossi V. Manganese-52 positron emission tomography tracer characterization and initial results in phantoms and in vivo. Med Phys. (2013) 40:042502. 10.1118/1.4793756. (Year: 2013).*

Velasco M, Diaz-Garcia CM, Larque C, Hiriart M. Modulation of ionic channels and insulin secretion by drugs and hormones in pancreatic beta cells. Mol Pharmacol. 2016; 90(3):341-357. doi: 10.1124/mol.116.103861. (Year: 2017).*

Roper MG, Qian WJ, Zhang BB, Kulkarni RN, Kahn CR, Kennedy RT Effect of the insulin mimetic L-783,281 on intracellular Ca2+ and insulin secretion from pancreatic beta-cells. Diabetes. 2002; 51:S43-S49. doi: 10.2337/diabetes.51.2007.S43. (Year: 2002).*

Rorsman P, Berggren PO, Hellman B. Manganese accumulation in pancreatic beta-cells and its stimulation by glucose. Biochem J. 1982;202(2):435-444. doi:10.1042/bj2020435. (Year: 1982).*

Lin, Mai et al. “Advances in molecular imaging of pancreatic beta cells” Frontiers in bioscience : a journal and virtual library vol. 13 4558-75. May 1, 2008 (Year: 2008).*

Lewis CM, et al. (2015) 52Mn production for PET/MRI tracking of human stem cells expressing divalent metal transporter 1 (DMT1). Theranostics 5(3):227. (Year: 2015).*

Rorsman, P, and B Hellman. “The interaction between manganese and calcium fluxes in pancreatic beta-cells.” The Biochemical journal vol. 210,2 (1983): 307-14. doi:10.1042/bj2100307 (Year: 1983).*

Wooten, A Lake et al. “Biodistribution and PET Imaging of pharmacokinetics of manganese in mice using Manganese-52.” PloS one vol. 12,3 e0174351. Mar. 17, 2017, doi:10.1371/journal.pone.0174351 (Year: 2017).*

Wooten et al., “Biodistribution and PET Imaging of pharmacokinetics of manganese in mice using Manganese-52” PLoS One 12(3): e0174351 pp. 1-14 (Year: 2017).*

Rorsman, et al., “Manganese Accumulation in Pancreatic B-cells and its Stimulation by Glucose”, Biochem. J., (1981) vol. 202, pp. 435-444 (Year: 1981).*

Lewis, et al., “52Mn Production for PET/MRI Tracking Of Human Stem Cells Expressing Divalent Metal Transporter 1 (DMT1)”, Theranostics, 2015; vol. 5 Is. 3 pp. 227-239. (Year: 2015).*

Antkowiak PF, et al. (2009) Noninvasive assessment of pancreatic beta-cell function in vivo with manganese-enhanced magnetic resonance imaging. Am J Physiol Endocrinol Metab 296(3):E573-578.

Antkowiak PF, et al. Manganese-enhanced magnetic resonance imaging detects declining pancreatic β-cell mass in a cyclophosphamide-accelerated mouse model of type 1 diabetes. Diabetes. 2013;62:44-48.

Antkowiak PF, et al. Quantitative pancreatic B cell MRI using manganese-enhanced Look-Locker imaging and two-site water exchange analysis. Magn Reson Med 2012;67:1730-1739.

Atkins HL, et al. (1979) Myocardial positron tomography with manganese-52m. Radiology 133(3Pt 1):769-774.

Au C, et al. Manganese transport in eukaryotes: the role of DMT1. Neurotoxicology 2008;29:569-576.

Bandara N, et al. (2016) Evaluation of Cu-64 and Ga-68 Radiolabeled Glucagon-Like Peptide-1 Receptor Agonists as PET Tracers for Pancreatic β cell Imaging. Mol Imaging Biol 18(1):90-98.

Bock T, et al. Increased islet vol. but unchanged islet number in ob/ob mice. Diabetes 2003;52:1716-1722.

Brunnquell CL, et al. Uptake and retention of manganese contrast agents for PET and MRI in the rodent brain. Contrast Media Mol. 2016;in press.

Buchholz M, et al. (2013) Cross-section measurements for the formation of manganese-52 and its isolation with a non-hazardous eluent. Radiochim Acta 101(8):491-499.

Buchholz M, et al. (2015) Optimized separation procedure for production of no-carrier-added radiomanganese for positron emission tomography. Radiochim Acta 103(12):893-899.

Crossgrove J, et al. Manganese toxicity upon overexposure. NMR Biomed 2004;17:544-553.

Eriksson O, et al. (2010) In vivo and in vitro characterization of [18 F]-FE-(+)-DTBZ as a tracer for beta-cell mass. Nucl Med Bio 37(3):357-363.

Eter WA, et al. (2015) Graft revascularization is essential for non-invasive monitoring of transplanted islets with radiolabeled exendin. Sci Rep 5:15221.

Fonslet et al., “Optimized Preparation of Manganese-52 from Chromium.” Appl. Rad. Iso., In Press. 2017.

Gotthardt M, et al. (2014) Beta cell imaging—a key tool in optimized diabetes prevention and treatment. Trends Endocrinol Metab 25(8):375-377.

Graves S, et al. (2016) Probing the impact of isoflurane on acute pancreatic function with 52Mn-PET. J Nucl Med 57 (supplement 2):167-167.

Graves SA, et al. (2015) Novel Preparation Methods of 52Mn for ImmunoPET Imaging. Bioconjug Chem 26 (10):2118-2124.

(56) References Cited

OTHER PUBLICATIONS

Graves, C.A., Production of positron-emitting isotopes of Manganese and Applications Thereof, Seminar Oct. 31, 2016.
Graves, S. A., et al. "Preparation and in vivo characterization of 51 MnCl 2 as PET tracer of Ca 2+ channel-mediated transport." Scientific reports 7.1 (2017): 3033.
Graves, S.A., et al. "Half-life of 51Mn." Physical Review C 96.1 (2017).
Hellman B, et al. Glucose induces oscillatory Ca2+ signalling and insulin release in human pancreatic beta cells. Diabetologia. 1994;37:S11-S20.
Hernandez R, et al. Radio-manganese PET imaging of pancreatic beta cells. Journal of Nuclear Medicine. 2016;57:5-5.
Hernandez, R., et al. "Radiomanganese PET detects changes in functional β-cell mass in mouse models of diabetes." Diabetes 66.8 (2017): 2163-2174.
Hernandez, R., et al., Radio-manganese PET imaging of Pancreatic beta cells, Presentation, San Diego, 2016.
Klein A, et al. Investigation of 50Cr (d, n) 51Mn and natCr (p, x) 51Mn processes with respect to the production of the positron emitter 51Mn. Radiochimica Acta. 2000;88:253.
Klein A, et al. Production of the positron emitter 51Mn via the 50Cr (d, n) reaction: targetry and separation of no-carrier-added radiomanganese. Radiochimica Acta. 2002;90:167-177.
Lahiri S, et al.(2006) Separation of No. carrier-added 52Mn from bulk chromium: a simulation study for accelerator mass spectrometry measurement of 53Mn. Anal Chem 78(21):7517-7521.
Lamprianou S, et al. (2011) High-resolution magnetic resonance imaging quantitatively detects individual pancreatic islets. Diabetes 60(11):2853-2860.
Lewis CM, et al. (2015) 52Mn production for PET/MRI tracking of human stem cells expressing divalent metal transporter 1 (DMT1). Theranostics 5(3):227.
Lin, Mai et al. "Advances in molecular imaging of pancreatic beta cells" Frontiers in bioscience : a journal and virtual library vol. 13 4558-75. May 1, 2008.
Merrins MJ, et al. (2016) Phase Analysis of Metabolic Oscillations and Membrane Potential in Pancreatic Islet beta-Cells. Biophys J 110(3):691-699.
Moore A: Advances in beta-cell imaging. Eur J Radiol 2009;70:254-257.
Rorsman P et al. (1983) The interaction between manganese and calcium fluxes in pancreatic B-cells. Biochem J 210 (2):307-314.
Rorsman P, et al. (1982) Manganese accumulation in pancreatic beta-cells and its stimulation by glucose. Biochem J 202(2):435-444.
Rorsman P, et al. Insulin granule dynamics in pancreatic beta cells. Diabetologia. 2003;46:1029-1045.
Schafer MK, et al. (2013) Species-specific vesicular monoamine transporter 2 (VMAT2) expression in mammalian pancreatic beta cells: implications for optimising radioligand-based human beta cell mass (BCM) imaging in animal models. Diabetologia 56(5):1047-1056.
Silva AC, et al (2004) Manganese-enhanced magnetic resonance imaging (MEMRI): methodological and practical considerations. NMR Biomed 17(8):532-543.
Topping GJ, et al (2013) Manganese-52 positron emission tomography tracer characterization and initial results in phantoms and in vivo. Med Phys 40(4):042502.
Vegas AJ, et al. (2016) Long-term glycemic control using polymer-encapsulated human stem cell-derived beta cells in mmune-competent mice. Nat Med 22(3):306-311.

* cited by examiner

METHODS FOR QUANTIFYING PANCREATIC BETA CELL FUNCTION AND MASS PROPERTIES WITH RADIOMANGANESE POSITRON EMISSION TOMOGRAPHY

CROSS-REFERENCE TO RELATED APPLICATIONS

This application claims the benefit of U.S. Provisional Patent Application Ser. No. 62/475,571, filed on Mar. 23, 2017, and entitled "METHODS FOR QUANTIFYING PANCREATIC BETA CELL FUNCTION AND MASS PROPERTIES WITH RADIOMANGANESE POSITRON EMISSION TOMOGRAPHY," which is herein incorporated by reference in its entirety.

STATEMENT REGARDING FEDERALLY SPONSORED RESEARCH

This invention was made with government support under CA169365 awarded by the National Institutes of Health. The government has certain rights in the invention.

BACKGROUND

Type 1 diabetes mellitus caused by the autoimmune destruction of insulin producing pancreatic beta cells affects approximately 0.2% of the world's population. Pancreatic islet transplantation combined with immune suppression has been shown to temporarily allow for partial or full insulin independence in patients with type 1 diabetes mellitus, but no permanent treatment yet exists. An imaging modality capable of monitoring the decline of functional beta cell mass and the viability of islet or stem-cell derived beta cell transplants would be invaluable to future therapeutic investigations.

Human pancreatic islets occupy approximately 4.5% of the pancreas volume, and are composed of a mixture of β, α, γ, δ, and ε cells. As individual islets vary in size from 25 to 400 μm in diameter and are non-uniformly distributed throughout the pancreas, quantification is challenging using noninvasive anatomical imaging techniques such as magnetic resonance imaging (MRI) or computed tomography (CT). Alternatively, positron emission tomography (PET) is a technique that typically involves quantifying the in vivo distribution of a biologically relevant moiety via tracking with a positron emitting radioisotope. Compared with MRI and CT, PET has significantly greater imaging sensitivity and inherently probes physiology rather than anatomy, which may prove useful in the clinical quantification of functional beta cell mass.

$Mn^{2+}$, in a behavior that mimics $Ca^{2+}$, is freely transported through voltage dependent $Ca^{2+}$ channels (VDCCs). Because VDCC activation is required for the release of insulin from beta cells, $Mn^{2+}$ has been proposed as a molecular imaging agent for probing beta cell function and mass using manganese-enhanced magnetic resonance imaging ("MEMRI"). However, this technique is limited by the significant cellular toxicity of $Mn^{2+}$ at the concentration necessary for increasing image contrast, and slow biological clearance of manganese, which prevents the possibility of repeated contrast administration.

SUMMARY OF THE DISCLOSURE

The present disclosure addresses the aforementioned drawbacks by providing a method for quantitatively imaging pancreatic beta cells using positron emission tomography ("PET"). Radiomanganese is administered to a subject. The radiomanganese can be free isotopes or can be linked or otherwise conjugated to other molecules. Data are acquired from a region-of-interest containing a pancreas of the subject using a PET system. An image of the region-of-interest is reconstructed from the acquired data. The reconstructed image depicts a preferential uptake of the radiomanganese in pancreatic beta cells in the subject. The image is processed with a computer system to estimate a quantitative parameter of one of pancreatic beta cell mass or pancreatic beta cell function.

It is another aspect of the disclosure to provide a method for imaging pancreatic beta cells using PET. A first image and a second image of a subject acquired with a PET system following administration of radiomanganese to the subject are provided to a computer system. The first image depicts a first radiomanganese activity in the subject and the second image depicts a second radiomanganese activity in the subject. A difference between the first activity and the second activity is computed and a pancreatic beta cell mass, such as a functional beta cell mass, is quantified based on the computed difference.

It is another aspect of the disclosure to provide a method for assessing a pancreatic tissue transplant using PET. Radiomanganese is administered to a subject who has received a pancreatic tissue transplant, which may be a stem cell-derived tissue transplant. An image of the subject is acquired with a PET system and a pancreatic beta cell mass is computed from the acquired image. A report is then generated based on the computed pancreatic beta cell mass. The report contains information associated with an assessment of transplant viability of the pancreatic tissue transplant.

It is yet another aspect of the disclosure that a pharmacological agent can be administered to the subject before administering radiomanganese, wherein the pharmacological agent modulates the uptake of divalent metals by pancreatic beta cells. The pharmacological agent can inhibit or stimulate divalent metal uptake.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 7A shows coronal PET images 1 h post injection showing the pancreas of mice given IP injections of diazoxide (20 mg/kg), nifedipine (20 mg/kg), or glibenclamide (5 mg/kg) prior to the administration of a $^{52}Mn^{2+}$ rapid bolus. Yellow arrows point to white contours demarcating the pancreas. FIG. 7B shows manual ROI-based quantification of static PET images acquired 1 h post injection. FIG. 7C shows results from ex vivo biodistribution studies following PET imaging. Significantly reduced pancreatic uptake of $^{52}Mn^{2+}$ is observed in mice that received nifedipine and diazoxide ($P<0.0001$) prior to radiotracer administration. Mice which received glibenclamide (5 mg/kg) prior to radiotracer administration had significantly higher pancreatic uptake of $^{52}Mn^{2+}$ than the control mice, in both PET ($P=0.02$) and biodistribution ($P=0.047$) studies. SG: salivary gland.

FIG. 8A shows that following the administration of an acute dose of streptozotocin (STZ, 180 mg/kg), ICR mice started to show symptoms of diabetes: reduced weight and high blood glucose level (BGL; >250 mg/dL). FIG. 8B shows one-hour post injection coronal PET images of healthy (left panel) or diabetic (center/right panels) ICR mice showing a reduced PET signal in the pancreas of the diabetic mice. The significant decline in $^{52}Mn^{2+}$ uptake in the pancreas of STZ-diabetic mice was confirmed quantitatively by ROI analysis of the PET images (FIG. 8C) and ex vivo biodistribution (mean±SD; ** $P<0.0001$; n=3) (FIG. 8D). SG: salivary gland.

FIG. 9A shows coronal PET images acquired 1 h after $^{52}Mn^{2+}$ administration. The pancreas can be readily delineated in the images of both obese (ob/ob) mice and lean (C57BL/6J) controls. Yellow arrows point to hand-drawn contours of the pancreas. FIG. 9B shows image-derived quantification expressed as SUV indicated a significant difference in $^{52}Mn^{2+}$ pancreatic uptake between groups (mean±S.D; *** $P<0.0001$; n=3). SG: salivary gland.

DETAILED DESCRIPTION

Figure 1:
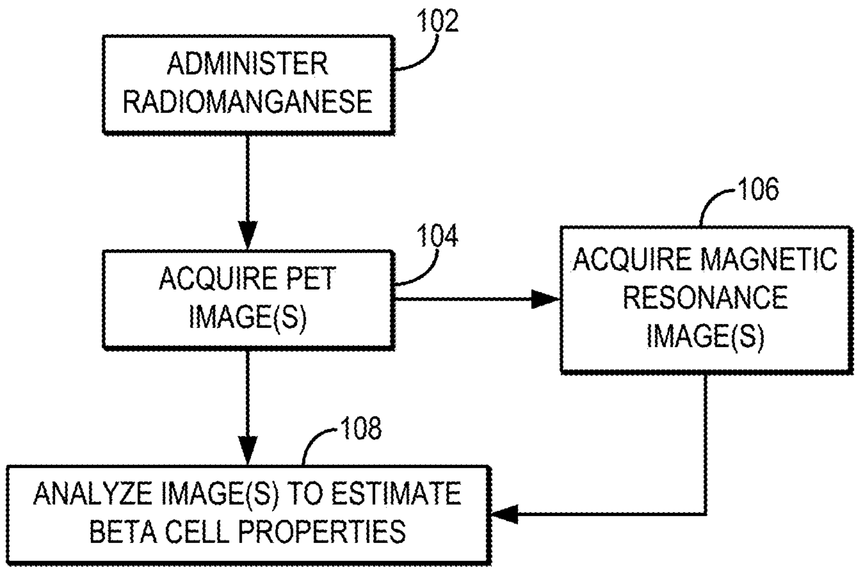
FIG. 1 is a flowchart setting forth the steps of an example method for estimating a property of pancreatic beta cells using radiomanganese positron emission tomography ("PET").

Described here are methods for imaging beta cells in pancreatic tissue using radioisotopes of manganese, which may be referred to as radiomanganese. Example radioisotopes of manganese include Mn-52g, Mn-52m, and Mn-51. As one example, radiomanganese can be used to image pancreatic beta cells, in which radiomanganese shows a preferential uptake. This provides for applications such as quantifying beta cell mass (e.g., functional beta cell mass), assessing transplant viability, monitoring the efficacy of drug treatments, and so on.

Radiomanganese is advantageous for positron emission tomography ("PET") imaging applications because of its favorable physical and chemical properties. As an example of its favorable chemical properties, radiomanganese can be rapidly and stably chelated by 1,4,7,10-tetraazacyclododecane-1,4,7,10-tetraacetic acid, which is also known as DOTA. This chelation enables bioconjugate applications of radiomanganese, including conjugating radiomanganese with antibodies, peptides, small molecules, whole cells, and so on. As another example of its favorable chemical properties, manganese can also be integrated into manganese-based nanoparticles, such as manganese-oxide nanopartides, manganese containing porphysomes, and so on.

The physical properties of radiomanganese enable different uses and applications based on the different isotopes used to form the radiomanganese. Table 1 illustrates some of the physical properties of the Mn-51, Mn-52m, and Mn-52g radioisotopes of manganese.

TABLE 1

| Isotopes of Manganese | | | |
|---|---|---|---|
| | Mn-51 | Mn-52m | Mn-52g |
| Half-Life | 45.6 minutes | 21 minutes | 5.6 days |
| $\beta^+$ Branch | 97% | 97% | 29% |
| $\beta^+$ Average Energy (keV) | 973 | 1172 | 242 |
| Gamma Ray Energies (keV) | — | 1434 | 744, 935, 1434, . . . |

Mn-52g has a long half-life relative to the other isotopes of manganese. This longer half-life makes Mn-52g less suitable for clinical use, but more advantageous for preclinical studies. For instance, the longer half-life means that Mn-52g radiomanganese can be shipped worldwide. Mn-52m has a relatively short half-life and produces unfavorable gammas. Although Mn-52m radiomanganese could be used for clinical use, it is more difficult to produce and handle than Mn-51. Mn-51 has a short half-life, a strong positron branch, and no prominent gammas. These properties make Mn-51 advantageous for clinical use.

Thus, in general, based on the physical properties of the different isotopes of manganese, it is contemplated that radiomanganese containing Mn-52g will be advantageous for preclinical studies, whereas radiomanganese containing Mn-51 will be more advantageous for clinical studies and use.

Another beneficial property of manganese is that it behaves biologically like $Ca^{2+}$, which enables its use in applications such as neural tract tracing, pancreatic beta cell imaging, measuring cardiac efflux rates for determining myocardial infarction, insulinoma imaging, and so on.

Radiomanganese also has the benefit of being a magnetic resonance imaging ("MRI") contrast agent that shortens the longitudinal relaxation time ("TI") of nuclear spins proximate the contrast agent. As a result of this property, radiomanganese can be advantageous for imaging studies that implement simultaneous PET/MRI.

An example of an existing manganese-based MRI contrast agent is Mangafodipir. A significant drawback to manganese-based MRI contrast agents is that these agents are cytotoxic, especially at the large amount of contrast agent that is necessary to achieve a suitable increase in image contrast. The slow excretion of manganese from contrast agents such as Mangafodipir also means that repeated imaging of a subject is not practical.

Because $MnCl_2$ has the same final biodistribution as Mangafodipir, radiomanganese containing $MnCl_2$ may provide complimentary diagnostic value in both PET imaging and MRI. As an added benefit, using radiomanganese containing $MnCl_2$ provides reduced toxicity to the subject as compared to the higher toxicity Mangafodipir. For instance, radiomanganese can provide a suitable image contrast at much lower doses than are required for manganese-based MRI contrast agents, such as Mangafodipir. As an example, radiomanganese can be administered with doses in a sub micromolar range, such as a picomolar ("pM") range, while still producing appreciable image contrast. The rapid blood clearance of radiomanganese containing $MnCl_2$ also enables rapid scanning.

As mentioned above, radiomanganese can be used for quantifying beta cell mass, such as by quantifying functional beta cell mass. The noninvasive determination of functional beta cell mass is very useful for monitoring the progression of type-1 and type-2 diabetes, as well as other applications including monitoring the viability of transplanted insulin-producing cells. Previous work implementing manganese-enhanced MRI has shown promise for beta cell mass determination through voltage-dependent calcium channel ("VDCC") internalization of $Mn^{2+}$. However, these methods require the injection of bulk cytotoxic manganese contrast agent, which limits the clinical utility of such methods.

In addition to imaging pancreatic beta cells and measuring properties associated with those cells, radiomanganese can be used for other applications, including immunoPET applications, DMT-1 reporter gene imaging, neural tract tracing, PET/MRI applications with radiomanganese-based nanoparticles, insulinoma imaging, porphysome imaging, cell tracking, and small molecule studies. These additional imaging applications can be used for imaging the pancreas or other tissues and organ systems, whether or not in connection with studying the pancreas. As one example, radiomanganese can be used in immunoPET applications by conjugating the radiomanganese with molecules used in immunotherapy treatments. The radiomanganese can be imaged with PET to monitor the efficacy of the immunotherapy. These applications may have specific utility for predinical studies.

The methods described in the present disclosure make use of radiomanganese and PET imaging to image the pancreas and to monitor the physical, chemical, physiological, or other properties of pancreatic beta cells. For instance, radiomanganese can be used to quantify beta cell mass, monitor pancreatic function, assess the viability of transplanted insulin-producing cells, evaluate the efficacy of drugs or other treatment schemes, and so on.

Referring now to FIG. 1, a flowchart is illustrated as setting forth the steps of an example method for quantifying pancreatic beta cell mass or function using radiomanganese PET. Radiomanganese is administered to a subject, as indicated at step 102. The radiomanganese can be administered as free isotopes of radiomanganese, or the radiomanganese can be linked to other molecules, such as by conjugation with an antibody or a peptide. In some instances, the radiomanganese can be administered as a compound that dissociates to produce free manganese when administered to the subject (e.g., in an in vivo environment). As one example, mangafodipir can slowly release manganese into the blood stream. Images are then obtained from the subject following administration of the radiomanganese, as indicated at step 104. While these images are preferably PET images, images can also be obtained with MRI, as indicated at step 106. In some applications, images can be acquired with an integrated PET/MRI system, which allows for simultaneous, or near-simultaneous, acquisition of both PET images and magnetic resonance images.

The images acquired from the subject following administration of radiomanganese are then analyzed to quantify the desired properties of pancreas, such as beta cell mass or beta cell functions, as indicated at step 108. Methods for processing the image are described below.

In some applications, a pharmacological agent can be administered to the subject to modulate divalent metal (and thus radiomanganese) uptake in pancreatic beta cells. Techniques such as these can be useful in beta cell mass (BCM) quantification studies for the subtraction of non-specific exocrine pancreas uptake by stimulation or blocking (e.g., through glibendamide or nifedipine) of beta cell VDCCs following baseline imaging. On the other hand, the pulsatile nature of calcium transport may increase test-retest variability for bolus injection techniques. This effect could possibly be mitigated by administering $^{51}MnCl_2$ as an intravenous infusion over 5-15 minutes.

Figure 2:
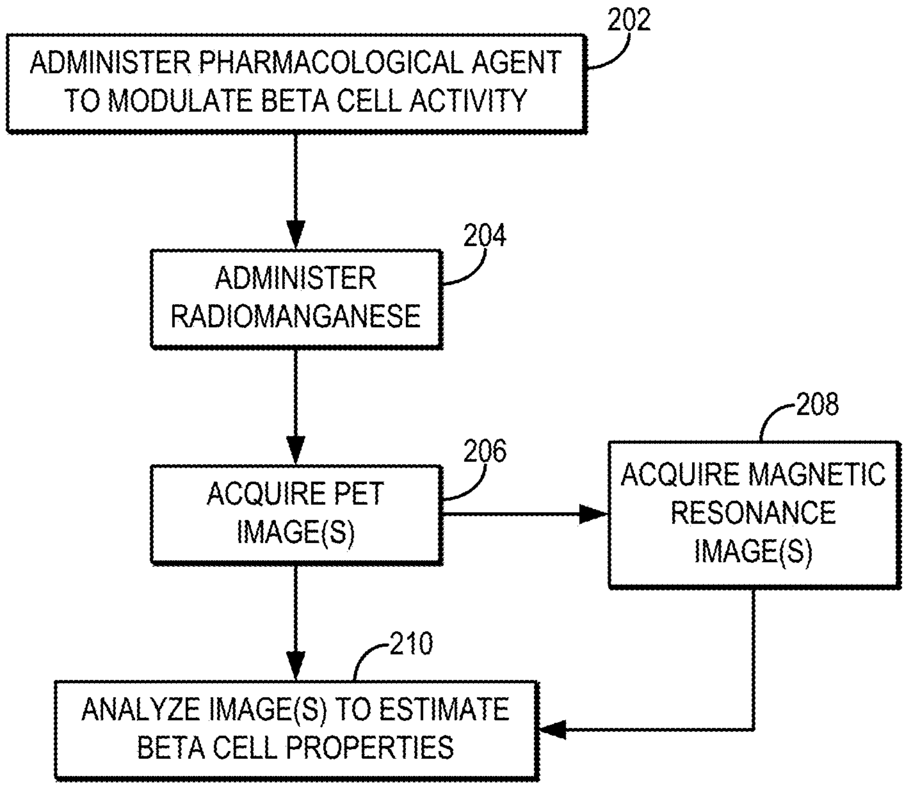
FIG. 2 is a flowchart setting forth the steps of an example method for estimating a property of pancreatic beta cells using radiomanganese PET following the pharmacological modulation of pancreatic beta cell function associated with divalent metal uptake.

Referring now to FIG. 2, a flowchart is illustrated as setting forth the steps of an example method for quantifying pancreatic beta cell mass or function using radiomanganese PET following administration of a pharmacological agent that modulates divalent metal uptake (e.g., $Ca^{2+}$ uptake) by pancreatic beta cells. The method thus includes administering a pharmacological agent to the subject, as indicated at step 202. The pharmacological agent can inhibit or stimulate the uptake of divalent metals by the pancreatic beta cells. Examples of such agents are discussed below in more detail.

Radiomanganese is then administered to the subject, as indicated at step 204. The radiomanganese can be administered as free isotopes of radiomanganese, or the radiomanganese can be linked to other molecules, such as by conjugation with an antibody or a peptide. Images are then obtained from the subject following administration of the radiomanganese, as indicated at step 206. While these images are preferably PET images, images can also be obtained with MRI, as indicated at step 208. In some applications, images can be acquired with an integrated PET/MRI system, which allows for simultaneous, or near-simultaneous, acquisition of both PET images and magnetic resonance images.

The images acquired from the subject following administration of radiomanganese are then analyzed to quantify the desired properties of pancreas, such as beta cell mass or beta cell functions, as indicated at step 210. Methods for processing the image are described below. For example, images with and without pharmacological modulation of radiomanganese uptake can be compared to quantify pancreatic beta cell function or mass. These comparisons may include computing the difference between two such images, correlating activities in one image with another, and so on. In some implementations, a report can be generated based on this comparison. For instance, the report may include numerical data indicating one or more quantitative values. As another example, the report may include an image, such as a digital image computed as a difference between two images. In this latter example, the report includes an image matrix having pixel values associated with difference values, which may be associated with a quantification of pancreatic beta cell function or mass.

Figure 3:
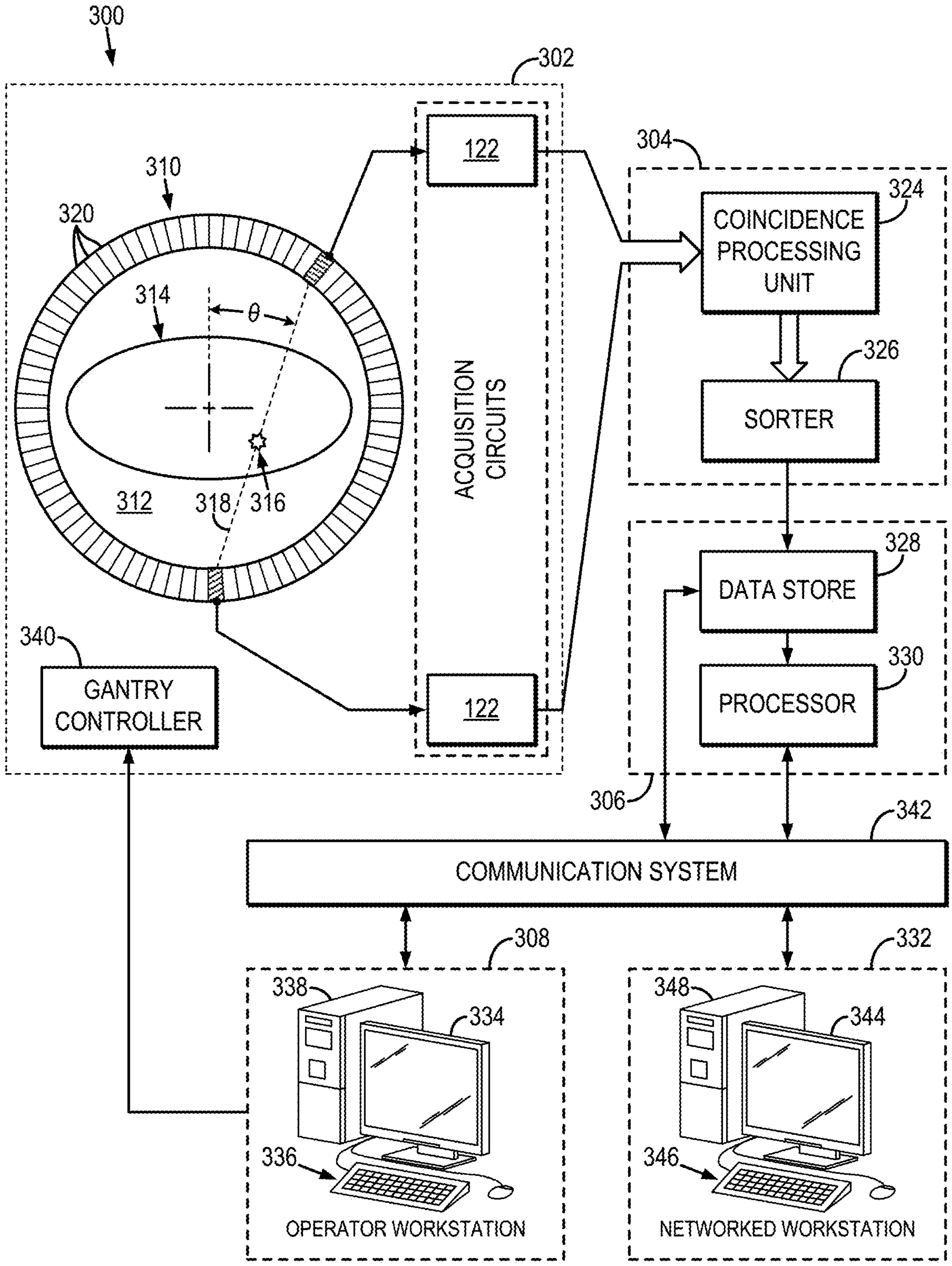
FIG. 3 is a block diagram of an example PET system that can be implemented with the methods described in the present disclosure.

Referring now to FIG. 3, an example of a positron emission tomography ("PET") system 300 that can be implemented with the methods described in the present disclosure is illustrated. The PET system 300 includes an imaging hardware system 302, a data acquisition system 304, a data processing system 306, and an operator workstation 308.

The imaging hardware system 302 generally includes a PET scanner having a radiation detector ring assembly 310 that is centered about the bore 312 of the PET scanner. The bore 312 of the PET scanner is sized to receive a subject 314 for examination. Prior to imaging, the subject 314 is administered a radioisotope, such as a radionuclide or radiotracer. As described in the present disclosure, the subject can be administered radiomanganese or a radiotracer or other agent containing radiomanganese. The subject may also be administered other pharmacological agents before imaging, such as pharmacological agents that modulate beta cell activity by suppressing or stimulating divalent metal uptake.

Positrons are emitted by the radiomanganese as it undergoes radioactive decay. These positrons travel a short distance before encountering electrons at which time the positron and electron annihilate. The positron-electron annihilation event 316 generates two photons that travel in opposite directions along a generally straight line 318.

The radiation detector ring assembly 310 is formed of multiple radiation detectors 320. By way of example, each radiation detector 320 may include one or more scintillators and one or more photodetectors. Examples of photodetectors that may be used in the radiation detectors 320 include photomultiplier tubes ("PMTs") or avalanche photodiodes ("APDs"). The radiation detectors 320 are thus configured to produce a signal responsive to the photons generated by annihilation events 316. The signal responsive to the detection of a photon is communicated to a set of acquisition circuits 322. The acquisition circuits 322 receive the photon detection signals and produce signals that indicate the coordinates of each detected photon, the total energy associated with each detected photon, and the time at which each photon was detected. These data signals are sent the data acquisition system 304 where they are processed to identify detected photons that correspond to an annihilation event 316.

The data acquisition system 304 generally includes a coincidence processing unit 324 and a sorter 326. The coincidence processing unit 324 periodically samples the data signals produced by the acquisition circuits 322. The coincidence processing unit 324 assembles the information about each detected annihilation event 316 into a set of numbers that indicate when the event took place and the position in which the event was detected. This event data is then processed by the coincidence processing unit 324 to determine if any two detected photons correspond to a valid coincidence event.

As one example, the coincidence processing unit 324 may determine if any two detected photons are in coincidence as follows. First, the times at which two photons were detected should be within a predetermined time window, for example, within 0-12 nanoseconds of each other, such as within a time window of 3-4 nanoseconds. Second, the locations at which the two photons were detected should lie on a line 318 that passes through the field of view in the PET scanner bore 312. Each valid coincidence event represents the line 318 connecting the two radiation detectors 320 along which the annihilation event 316 occurred, which is referred to as a line-of-response ("LOR"). The data corresponding to each identified valid coincidence event is stored as coincidence data, which represents the near-simultaneous detection of photons generated by an annihilation event 316 and detected by a pair of radiation detectors 320.

The coincidence data are communicated to a sorter 326 where the coincidence events are grouped into projection images, which may be referred to as sinograms. The sorter 326 sorts each sinogram by the angle of each view, which may be measured as the angle, $\theta$, of the line-of-response 318 from a reference direction that lies in the plane of the detector ring assembly 302. For three-dimensional images, the sorter 326 may also sort the sinograms by the tilt of each view. The sorter 326 may also process and sort additional data corresponding to detected photons, including the time at which the photons were detected and their respective energies.

After sorting, the sinograms are provided to the data processing system 306 for processing and image reconstruction. The data processing system 306 may include a data store 328 for storing the raw sinogram data. Before image reconstruction, the sinograms may undergo preprocessing to correct for random and scatter coincidence events, attenuation effects, and other sources of error. The stored sinogram data may thus be processed by a processor 330 located on the data processing system 306, by the operator workstation 308, or by a networked workstation 332.

The operator workstation 308 typically includes a display 334; one or more input devices 336, such as a keyboard and mouse; and a processor 338. The processor 338 may include a commercially available programmable machine running a commercially available operating system. The operator workstation 308 provides the operator interface that enables scan prescriptions to be entered into the PET system 300. In general, the operator workstation 308 may be in communication with a gantry controller 340 to control the positioning of the detector ring assembly 310 with respect to the subject 314 and may also be in communication with the data acquisition system 304 to control operation of the imaging hardware system 302 and data acquisition system 304 itself.

The operator workstation 308 may be connected to the data acquisition system 304 and data processing system 306 via a communication system 342, which may include any suitable network connection, whether wired, wireless, or a combination of both. As an example, the communication system 342 may include both proprietary or dedicated networks, as well as open networks, such as the internet.

The PET system 300 may also include one or more networked workstations 332. By way of example, a networked workstation 332 may include a display 344; one or more input devices 346, such as a keyboard and mouse; and a processor 348. The networked workstation 332 may be located within the same facility as the operator workstation 308, or in a different facility, such as a different healthcare institution or clinic.

The networked workstation 332, whether within the same facility or in a different facility as the operator workstation 308, may gain remote access to the data processing system 306 or data store 328 via the communication system 342. Accordingly, multiple networked workstations 332 may have access to the data processing system 306 and the data store 328. In this manner, sinogram data, reconstructed images, or other data may be exchanged between the data processing system 306 or the data store 328 and the networked workstations 332, such that the data or images may be remotely processed by a networked workstation 332. This data may be exchanged in any suitable format, such as in accordance with the transmission control protocol ("TCP"), the internet protocol ("IP"), or other known or suitable protocols.

Example: In Vivo Whole-Body PET and Biodistribution of $^{52}Mn^{2}$ in Normal Mice In this example, the in vivo biodistribution of $^{52}Mn^{2+}$ was investigated noninvasively with PET imaging. This example study also assessed the feasibility of using Mn-PET to probe beta cell mass and function.

Materials and Methods

Manganese-52 Production and Purification

Mn-52 was produced as described by S. A. Graves, et al., in "Novel Preparation Methods of $^{52}Mn$ for ImmunoPET Imaging," *Bioconjug. Chem.*, 2015; 26:2118-2124. Aliquots of the buffered $^{52}Mn$ solution (0.01M NaOAc, pH 6.5) were diluted to the desired injection volume (~200 µl) with phosphate-buffered saline (PBS), typically 2-4 MBq (50-100 µCi) per subject.

Animal Models

Two strains of mice, ICR (Envigo, Indianapolis, IN) and C57BL/6J (The Jackson Laboratory, a Harbor, ME), were employed for in vivo imaging studies. All mice were approximately ten weeks of age at the time of the experiments. Pre-diabetic C57BL/6J ob/ob mice carrying the homozygous obese spontaneous leptin mutation were obtained from the Jackson Laboratory. Mice had access to food and water ad libitum, except under fasting condition when access to food was restricted for 6-12 hours. All animal experiments were performed under the approval of the University of Wisconsin Institutional Animal Care and Use Committee.

PET Imaging

The acquisition of PET images was performed in the Inveon µPET/µCT scanner (Siemens Preclinical Solutions, Knoxville, TN). To study the long-term biodistribution and clearance of $^{52}Mn^{2+}$ in the mouse body, approximately 3.7 MBq (100 µCi) of $^{52}Mn^{2+}$ was injected intravenously (IV) in female ICR mice. Due to the long physical half-life of $^{52}Mn$ ($t_{1/2}$: 5.6 d), PET scans were recorded at multiple time-points between 1 hour and 13 days post injection of the radiotracer. Before each scan, mice were anesthetized with isoflurane (4% induction; 1% maintenance) and placed in the scanner in prone position. $30\times10^{6}$-$40\times10^{6}$ coincidence events per mouse static PET scans were acquired (time window, 3.432 ns; energy window, 350-650 keV) and the PET images were reconstructed in Inveon Acquisition Workplace (Siemens Preclinical Solutions, Knoxville, TN) workstation using a non-scatter-corrected three-dimensional Ordered Subset Expectation Optimization/Maximum a Posteriori (OSEM3D/MAP) algorithm. Region-of-interest (ROI) analysis was performed after organs were manually delineated on the PET images. Tissue uptake values were reported as standardized uptake value (SUV), which is normalized to whole body radiomanganese concentration.

To acquire dynamic PET scans, mice were anesthetized with isoflurane and the lateral tail vein was catheterized. Simultaneous with the administration of approximately 1.7 MBq (50 µCi) of $^{52}Mn^{2+}$ as a fast IV bolus, one-hour scans were recorded and list-mode files were binned into 46 frames (12×5 s, 6×10 s, 6×30 s, 10×60 s, 6×150 s, 6×300 s) and the images reconstructed using a non-scatter-corrected OSEM3D/MAP algorithm. In another study, 1.7 MBq (50 µCi) of $^{52}Mn^{2}$ was continuously infused with a syringe pump (Kd Scientific, Model 780100) over a period of 30 min, starting at the beginning of the PET scan. List-mode files were framed into 30×2 min frames and reconstructed using the above-mentioned algorithm.

To investigate the specificity of $^{52}Mn^{2+}$ for beta cells, a series of studies were performed where $^{52}Mn^{2+}$ uptake was manipulated through the pharmacologic stimulation or inhibition of the insulin secretory pathway. In these experiments, 0.74-1.85 MBq (20-50 µCi) of $^{52}Mn^{2+}$ was administered IV into either female ICR or C57BL/6J mice and static PET scans were acquired at one hour post injection. During tracer administration, mice were awake. Mice were only anaesthetized by isoflurane (1%) immediately before PET imaging.

Ex Vivo Biodistribution Studies

Ex vivo biodistribution studies were performed in all groups of mice in order to validate the results of PET imaging and obtain a more complete biodistribution profile of $^{52}Mn^{2+}$. Following the last imaging time point, mice were euthanized by $CO_2$ asphyxiation and the organs of interest were removed, wet-weighed, and counted on an automated gamma-counter (Wizard 2480, Perkin Elmer). The tissue uptake of $^{52}Mn^{2+}$ was reported as SUV (mean±SD).

Islet Isolation

Mouse pancreatic islets were isolated by collagenase digestion. Briefly, mice were placed under shallow anesthesia and sacrificed via cervical dislocation. The mouse common bile duct was cannulized and 3-5 mL of an ice-cold solution containing type XI collagenase (0.5 mg/mL; Sigma Aldrich, St. Louis, MO) and bovine serum albumin (BSA; 0.2 mg/mL; Sigma Aldrich, St. Louis, MO) in Hank's balanced salt solution (HBSS; Invitrogen, Carlsbad, CA) was injected into the mouse pancreas. After inflation, the pancreas was removed, placed in a glass vial containing 5 mL of the collagenase solution, and incubated in a shaking water bath at 37° C. Samples were digested for approximately 30 min after which the digests were centrifuged at 50×g for 2 min and islet pellets were washed three times with 30 mL of an ice-cold BSA (0.2 mg/mL) in HBSS solution. The pellet was resuspended and islets handpicked into 35 mm petri dishes. Following isolation, islets were placed in RPMI1640 media supplemented with penicillin (100 U/mL; Invitrogen), streptomycin (100 μg/mL; Invitrogen), and FBS [10% (wt/vol); Sigma] and incubated overnight at 37° C. in a 5% CO2 atmosphere.

Pharmacological Disruption of $^{52}Mn^{2+}$ Uptake in Islets of Langerhans

The uptake of $^{52}Mn^{2+}$ by murine islets of Langerhans was determined under several stimulatory or inhibitory conditions. Batches of 50 islets were transferred into 0.45 μm filtered bottom 1 mL centrifuge vials (Thermo Fisher Scientific, Grand Island, NY), 500 μL of Krebs-Ringer buffer (KRB: 118 mM NaCl, 5.4 mM KCl, 2.4 mM CaCl, 1.2 mM $MgSO_4$, 1 mM $KH_2PO_3$, 20 mM HEPES; pH 7.4) containing a low glucose concentration (1 mM D-glucose) were added and the islets incubated for 30 min at 37° C. After removing the supernatant following centrifugation at 50×g for 5 min, 250 μL of KRB containing glucose, diazoxide (50 μM; Tocris Biosciences, Bristol, UK), or tolbutamide (250 μM; Selleckchem, Houston, TX) were added, and the vials were spiked with 370 kBq (10 μCi) of $^{52}Mn^{2+}$. After 15 min of incubation, the solutions were filtered and islets were washed three times with KRB. The $^{52}Mn^{2+}$ radioactivity in the islet pellets were measured in an automated gamma counter (Perkin Elmer).

Stimulatory Effect of Glucose and Glibenclamide on Beta Cell Uptake of $^{52}Mn^{24}$ In Vivo To corroborate the correlation between $^{52}Mn^{2+}$ pancreatic uptake and the mechanism of insulin release in beta cells, the insulin secretory pathways were stimulated in vivo using glucose and glibendamide (Tocris Biosciences, Bristol, UK), which promotes insulin release in beta cells via blockade of ATP-sensitive potassium channel (KATP). Mice were injected intraperitoneally (IP) with 100 μL of glucose (1 g/kg) or glucose (1 g/kg)+glibenclamide (5 mg/kg) in PBS, 15 min before the IV injection of 0.74-1.85 MBq (20-50 μCi)$^{52}Mn^{2+}$. Static PET scans were acquired one hour after the injection of the radiotracer, after which ex vivo biodistribution was performed.

Inhibitory Effect of Diazoxide and Nifedipine on Beta Cell Uptake of $^{52}Mn^{2+}$ In Vivo VDCC blockade was achieved in vivo via a 20 mg/kg IP injection of 3,5-dimethyl 2,6-dimethyl-4-(2-nitrophenyl)-1,4-dihydropyridine-3,5-dicarboxylate (nifedipine; MP Biomedicals, LLC, Santa Ana, CA) in dimethyl sulfoxide. To activate KATP channels, mice received an IP injection of a 20 mg/kg dose in PBS of 7-Chloro-3-methyl-4H-1,2,4-benzothiadiazine 1,1-dioxide (diazoxide; Tocris Biosciences, Bristol, UK), a clinically used potent KATP agonist Both groups of mice were injected with 0.74 MBq (20 μCi) of $^{52}Mn^{2}$+, 15 min after the administration of either nifedipine of diazoxide. Whole-body PET scans were acquired at one hour post injection, after which ex vivo biodistribution was performed.

PET Studies in Type-1 Diabetes Model

Type 1 diabetes was induced in female ICR mice via a single IP injection of 180 mg/kg streptozotocin (STZ; MP Biomedical, LLC, Santa Ana, CA), a toxin that selectively destroys pancreatic beta cell. The injectable STZ solution (12.5 mg/mL) was prepared freshly in phosphate buffered saline (PBS). The weight of each mouse was measured daily, and blood glucose levels were recorded every other day with a glucometer (TRUEresult, Trividia Health Inc., Fort Lauderdale, FL) using blood samples collected from the tail vein. Mice were considered diabetic after two consecutive blood glucose readings above 250 mg/dL and were used for PET imaging studies one week after the injection of STZ. To evaluate $^{52}Mn^{2+}$ pancreatic uptake on diabetic mice, 0.74 MBq (20 μCi) of activity were administered IV and static PET images recorded one hour after administration of the tracer. Ex vivo biodistribution was carried out following PET acquisition.

PET Studies in Pre-Type 2 Diabetes Model

Given the altered glucose metabolism in obese mice, we compared the pancreatic uptake of $^{52}Mn^{2+}$ in lean (wild-type) and obese (ob/ob) mice on the C57BL/6J background. For PET imaging, 0.74 MBq (20 μCi) of $^{52}Mn^{2+}$ was IV injected into obese mice or lean controls one hour prior to PET scan acquisition. Subsequent $^{52}Mn^{2+}$ accumulation in the pancreas and other organs of interest was quantified.

Statistical Analysis

A minimum sample size of three (n=3) was used in all in vitro and in vivo experiments. The uptake of $^{52}Mn^{2+}$ in the different tissues was reported as SUV (mean±SD) and the differences between groups were evaluated for significance using a two-tailed Student's t-test. Differences were considered statistically significant at $P<0.05$.

Results

Mn-52 Production and Separation

Production yields of up to 5.92 MBq/μAh (355 MBq/h @ 60 ρA) were achieved using a $^{nat}$Cr pellet pressed into a silver disc substrate. Mn-52 was eluted in <1 mL of 0.01 M NaOAc buffer (pH~6.5) from a ~150 mg AG 1×8 column which had been previously rinsed with ethanol. Thin layer chromatographs confirmed the Mn(II) oxidation state following elution. End of bombardment radionuclidic purity was measured to be >99.5% by efficiency-calibrated high-purity germanium (HPGe) gamma spectrometry measurements. The only radionudidic impurity observed was <0.5% Mn-54 ($t_{1/2}$=312.1 d), which does not decay by positron emission.

In Vivo Whole-Body PET and Biodistribution of $^{52}Mn^{2}$ in Normal Mice

Figures 4A, 4B, 4C:
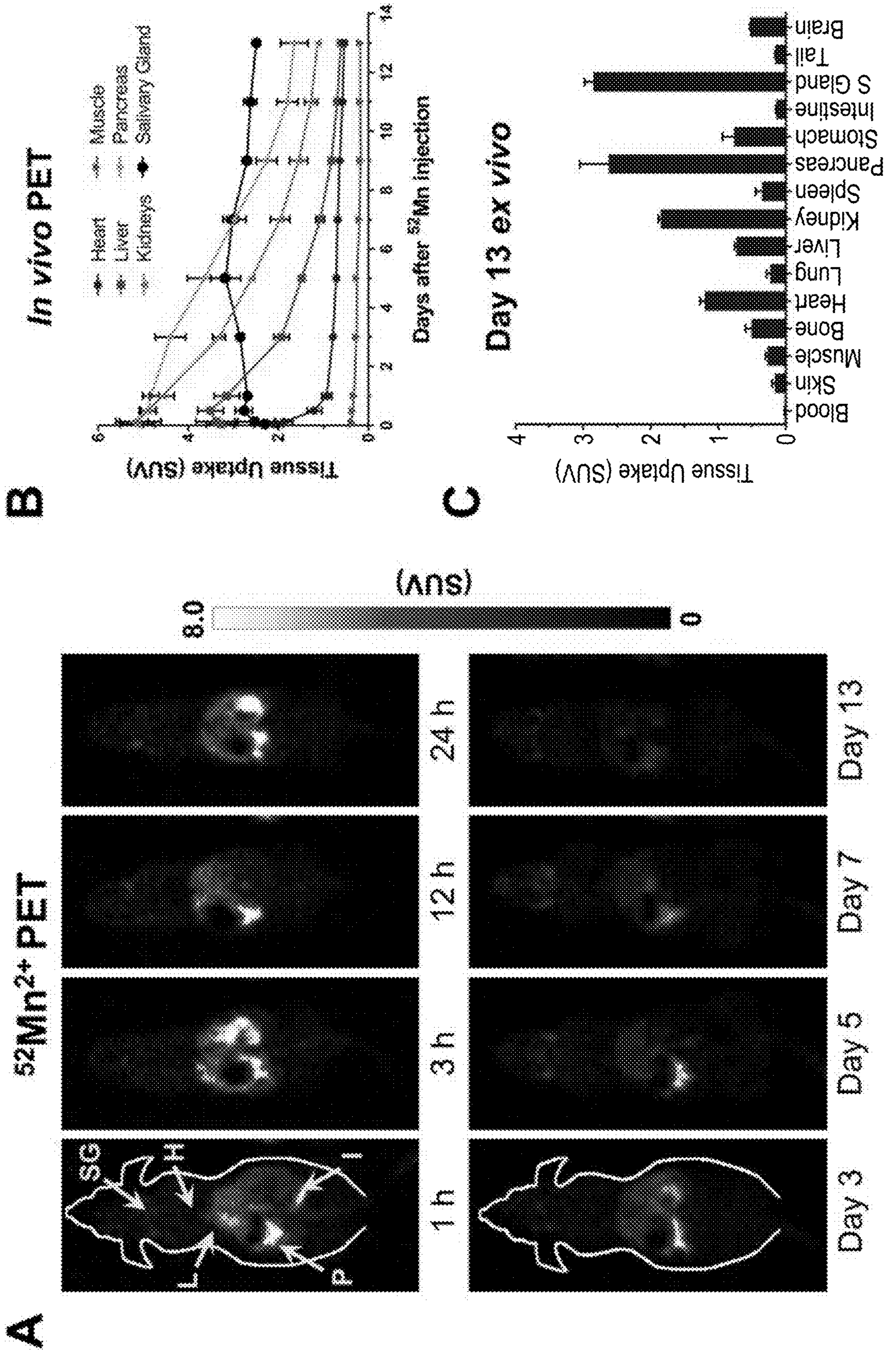
FIG. 4A shows serial PET images of ICR mice injected intravenously with $^{52}Mn^{2+}$ (no anesthesia except during the PET scans) in an example study. Coronal PET image slices were selected to best show pancreatic uptake. Arrows point to P: pancreas, H: heart, L: liver, I: intestines, and SG: salivary gland.
FIG. 4B shows ROI-based uptake quantification of the heart, liver, kidneys, muscle, pancreas, and submandibular salivary gland in an example study.
FIG. 4C shows ex vivo $^{52}Mn^{2+}$ biodistribution of sacrificed mice following last PET time-point, determined by gamma counting, in an example study. S Gland: salivary gland. n=4.

The in vivo biodistribution of $^{52}Mn^{2+}$ was investigated noninvasively with PET and ex vivo gamma counting. FIG. 4A shows coronal planes intersecting the pancreas of ICR mice, in PET scans acquired between 1 hour and 13 days after the IV injection of 3.7 MBq (100 μCi) of $^{52}Mn^{2+}$. A fast and prominent accumulation of $^{52}Mn^{2+}$ was observed in the pancreas, kidneys, liver, heart, and salivary glands (5.13±0.38, 5.13±0.02, 3.27±0.36, 2.11±0.20, and 2.30±0.26 SUV at 1 h post injection, respectively; n=3; FIG. 4B). In the subsequent time points during the longitudinal study, $^{52}Mn^{2+}$ accretion gradually declined in all organs except the salivary gland where uptake remained at around 3 SUV (FIG. 4B). $^{52}Mn^{2+}$ uptake in the pancreas, which was highest at 1 h post injection, was notably higher than in the liver and kidneys at all time points, with pancreas-to-normal organ contrast ratios peaked three days after $^{52}Mn^{2+}$ administration. Uptake in the muscle was very low and had little variation during the whole study. Ex vivo biodistribution was performed after the last PET scan 13 days after injection, confirming a marked accumulation of $^{52}Mn^{2+}$ in the salivary gland, pancreas, kidneys, and to a lesser extent, the heart and liver (FIG. 4C). Other organs including the brain, lungs, bones, intestines, stomach, and spleen displayed low $^{52}Mn^{2+}$ uptake, typically less than 0.5 SUV.

Figure 5:
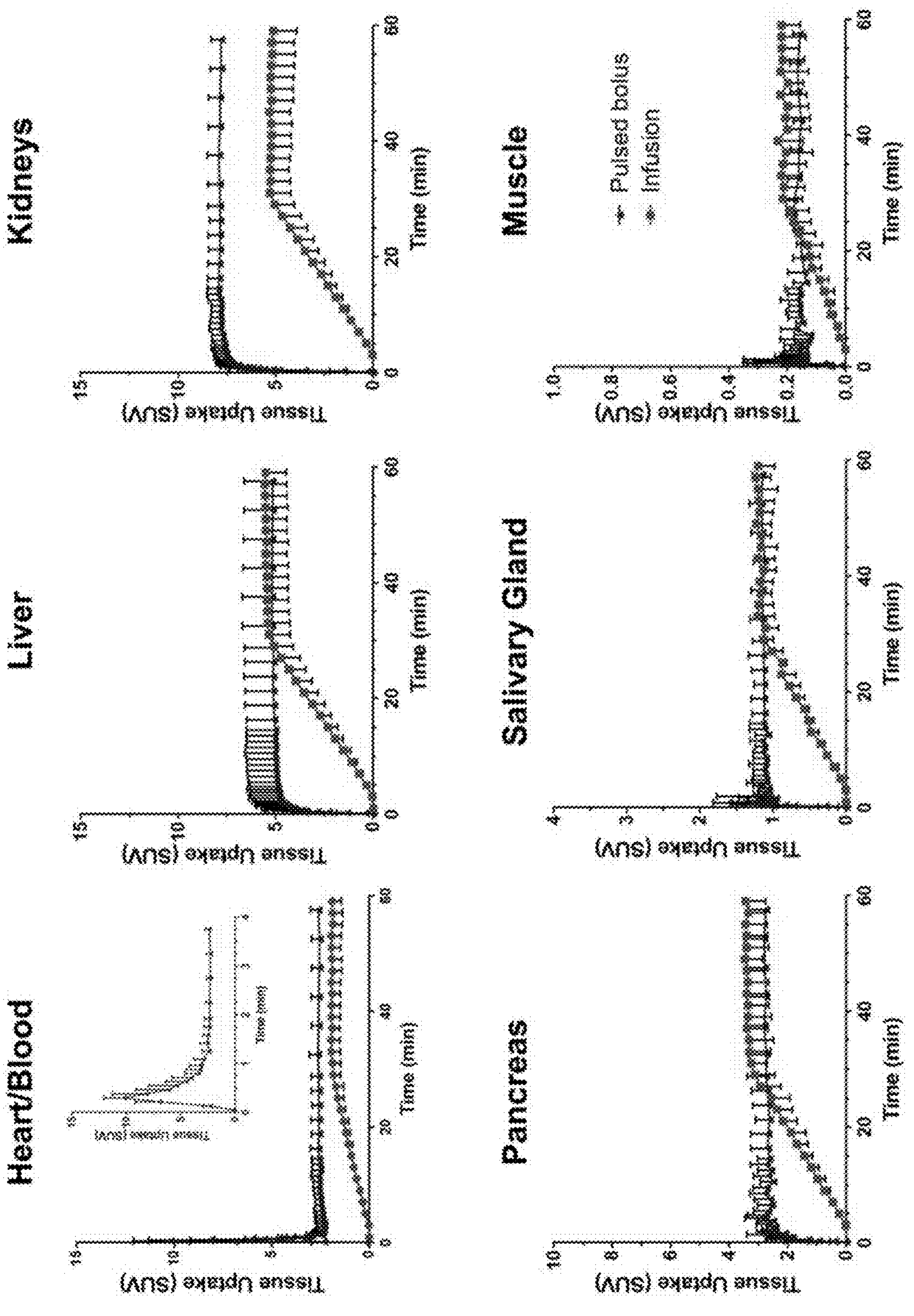
FIG. 5 shows dynamic PET time-activity curves (TACs) derived from hand-drawn ROIs for the heart/blood, liver, kidneys, pancreas, salivary gland, and muscle in an example study. Blue curves indicate TACs in mice injected by a rapid IV bolus of $^{52}Mn^{2}$, while red curves indicate an IV infusion of $^{52}Mn^{2+}$ over 30 minutes.

Because the whole-body distribution of $^{52}Mn^{2+}$ occurred largely within the first hour after IV administration (FIGS. 4A-4C), a dynamic PET study was designed to investigate the first hour of $^{52}Mn^{2+}$ kinetics. FIG. 5 shows the time-activity curves (TACs) resulting from ROI analysis of the dynamic PET data corresponding to the heart, liver, kidneys, pancreas, salivary gland, and muscle under two administration regimes: IV rapid bolus injection and IV continuous infusion over 30 minutes. The analysis of the myocardial TAC revealed extremely fast blood extraction kinetics with a blood circulation half-life of 10.7±3.5 s in mice administered a rapid IV $^{52}Mn^{2+}$ bolus. Consequently, $^{52}Mn^{2+}$ uptake was stabilized in the organs of interests within five minutes post injection. A residual radioactivity of 2.60±0.41 SUV was observed in the heart at one hour post injection, which was consistent with the specific uptake on $Mn^{2+}$ ions by myocardial tissue. Compared to the static one hour post injection PET scans, similar $^{52}Mn^{2+}$ uptake values were observed in the heart (2.11±0.20 vs. 2.60±0.41 SUV) and muscle (0.38±0.03 vs 0.16±0.02 SUV), while liver (3.27±0.34 vs. 5.16±1.46 SUV) and kidneys (5.13±0.02 vs. 7.81±0.51 SUV) were much higher at the end of the dynamic scan. Interestingly, a ~50% reduction in pancreatic uptake from 5.13±0.38 to 2.74±0.59 SUV was observed in the dynamic studies.

As is shown in FIG. 5 by the square data points, a continuous infusion of $^{52}Mn^{2+}$ over a 30 min time period resulted in a linear ramping in organ radioactivity, followed by an immediate plateau upon infusion termination. This corroborated the rapid distribution kinetics of $^{52}Mn^{2+}$. Comparable results were obtained by either rapid bolus (triangle data points) or continuous infusion (square data points) of $^{52}Mn^{2+}$ in terms of organ uptakes at equilibrium. Only the kidney displayed higher radioactivity at one hour post injection in mice administered the rapid bolus versus mice receiving continuous $^{52}Mn^{2+}$ infusion, 7.81±0.51 vs. 5.14±1.21 SUV, respectively (n=4). During the continuous infusion regime, pancreas reached an uptake of 3.44±0.69 SUV which, similar to the rapid bolus injection, was also significantly lower than that in the static PET scans at one hour post injection (5.13±0.38 SUV).

Previous reports have shown that most volatile anesthetics, including isoflurane, impair insulin secretion by inhibiting the deactivation of KATP channels. Plausibly, the observed decrease in pancreatic uptake of $^{52}Mn^{2+}$ resulted from mice being anesthetized through the full extent of the studies during the dynamic PET scans. To investigate the impact of isoflurane anesthesia on pancreatic uptake, one hour post injection biodistribution experiments were performed under different administration conditions in either anesthetized (1% isoflurane) or awake mice. Isoflurane significantly inhibited the accumulation of $^{52}Mn^{2+}$ in the pancreas regardless of the administration regime (e.g., rapid bolus, continuous infusion) or glucose stimulation, suggesting that isoflurane indeed acts as an indirect VDCC inhibitor via the upstream inhibition of KATP channel closure.

Uptake of $^{52}Mn^{2}$ in Isolated Islets

Figures 6A, 6B:
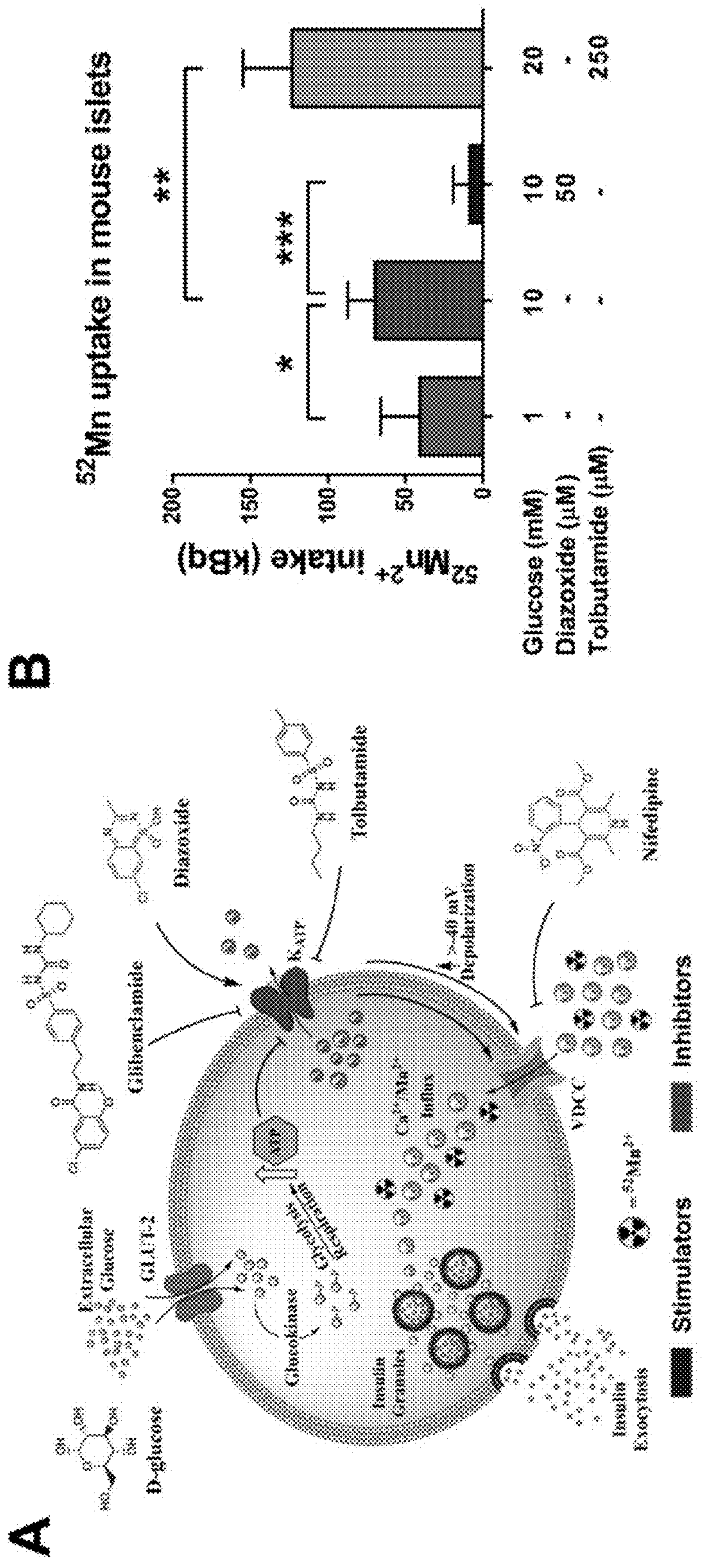
FIG. 6A illustrates pharmacologic manipulation of the insulin secretory pathway in beta cells. Molecular structures in blue indicate compounds which activate calcium influx through VDCC, while those in red are inhibitory.
FIG. 6B shows uptake of $^{52}Mn^{2+}$ by isolated ob/ob mouse islets in an example study. Groups of 50 islets from 3 independent islet preparations were incubated with $^{52}Mn^{2+}$ (370 kBq) in the presence of glucose and KATP channel modulators as indicated. Mean±S.D. *, $P<0.05$; , $P<0.01$; *, $P<0.001$.

To corroborate the mechanism of $^{52}Mn^{2+}$ uptake in the pancreas and its specificity for beta cells, an in vitro $^{52}Mn^{2+}$ uptake study was performed in islets isolated from obese (ob/ob) mice. Due to the similarities between $Mn^{2+}$ and $Ca^{2+}$ ions, $Mn^{2+}$ uptake by beta cells occurs via influx through VDCC (FIG. 6A). Isolated islets were incubated with 0.37 MBq (10 μCi) of $^{52}Mn^{2+}$ under several stimulatory/inhibitory conditions (FIG. 6B). $^{52}Mn^{2+}$ was readily taken up by islets, even under low glucose (1 mM) resting conditions. $^{52}Mn^{2+}$ uptake was significantly enhanced ($P<0.05$) when the islets were stimulated with 10 mM glucose. This effect was blocked by the further addition of diazoxide (50 μM), which inhibits the opening of VDCC via activation of KATP channels. As expected for intracellular $Ca^{2+}$, $^{52}Mn^{2+}$ uptake declined to levels well under the basal conditions. Conversely, glucose and the KATP channel blocker tolbutamide (250 μM) resulted in significantly higher $^{52}Mn^{2+}$ retention. Overall, these experiments demonstrate that pancreatic islet uptake of $^{52}Mn^{2+}$ depends on the activation status of beta cells.

Pharmacological Manipulation of $^{52}Mn^{24}$ Pancreatic Uptake In Vivo

Figures 7A, 7B, 7C:
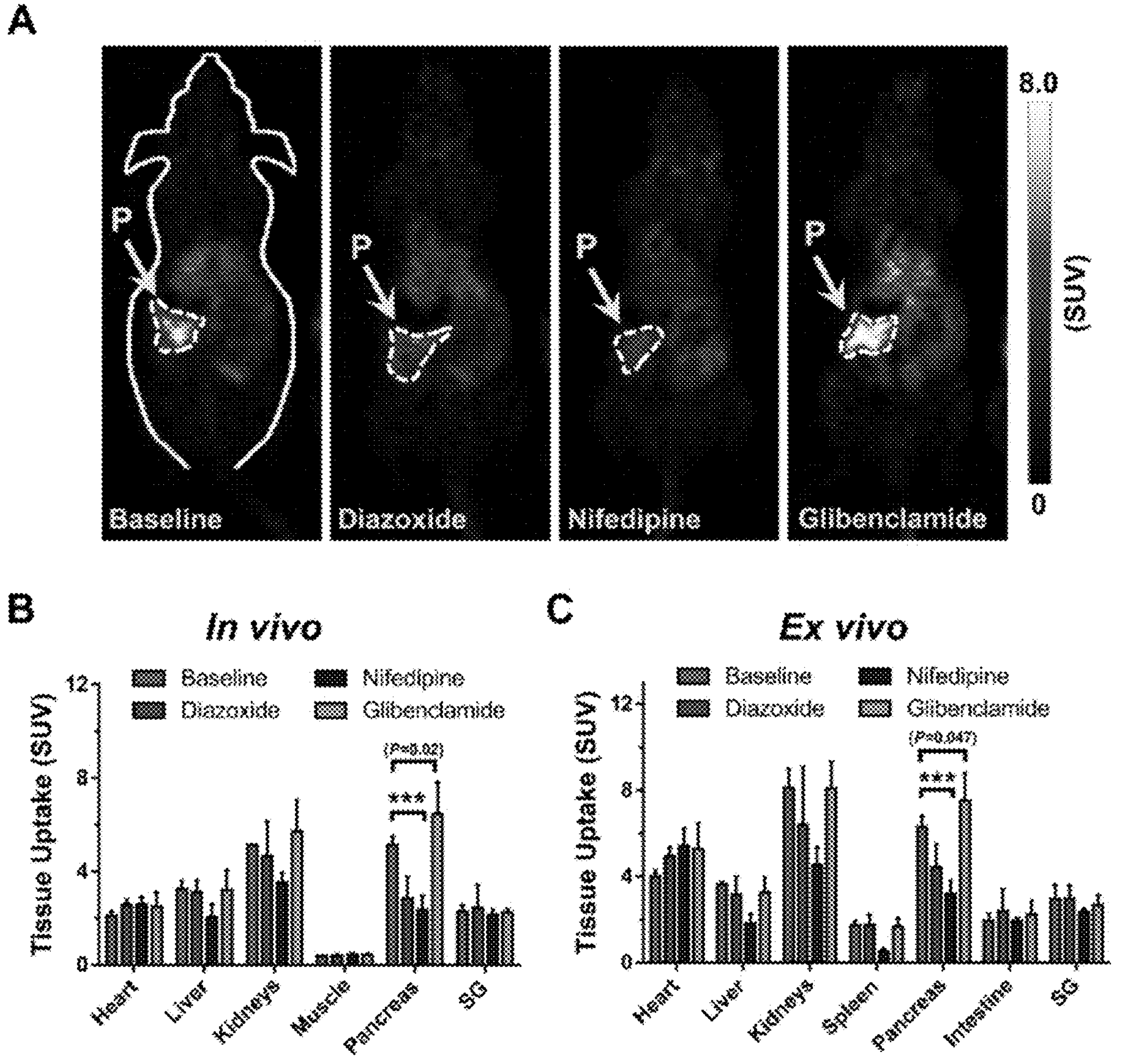
FIGS. 7A-7C show in vivo pharmacological modulation of $^{52}Mn^{2+}$ pancreatic uptake in ICR mice in an example study.

To verify the specificity of $^{52}Mn^{2+}$ accretion in the pancreas noninvasively using PET imaging, $^{52}Mn^{2+}$ pancreatic uptake was pharmacologically manipulated in vivo through the inhibition or stimulation of insulin secretion. In line with the in vitro results, inhibition of VDCC by direct blockade with nifedipine, or activation of KATP with diazoxide resulted in a significant ($P<0.0001$) abrogation of the PET signal within the pancreas. FIG. 7A shows coronal PET slices of the pancreas of ICR mice receiving 20 mg/kg IP injections of nifedipine or diazoxide, 10-15 min before the administration of an intravenous $^{52}Mn^{2+}$ bolus. Compared to the control group, a decrease in pancreatic PET signal was observed one hour following injection of $^{52}Mn^{2+}$ PET quantification revealed a 44% (5.13±0.36 vs. 2.85±0.92 SUV) and 54% (5.13±0.36 vs. 2.36±0.61 SUV) decline in $^{52}Mn^{2+}$ uptake in groups administered diazoxide and nifedipine, respectively (FIGS. 7B and 7C). On the contrary, mice administered glibenclamide (5 mg/kg) exhibited a significant enhancement in pancreatic SUV values. The distribution of $^{52}Mn^{2+}$ in other organs of interest including the heart, liver, kidneys, spleen and salivary gland remained largely unaltered among groups.

$^{52}Mn^{2+}$ Uptake in Type-1 Diabetic Mice

Figures 8A, 8B, 8C, 8D:
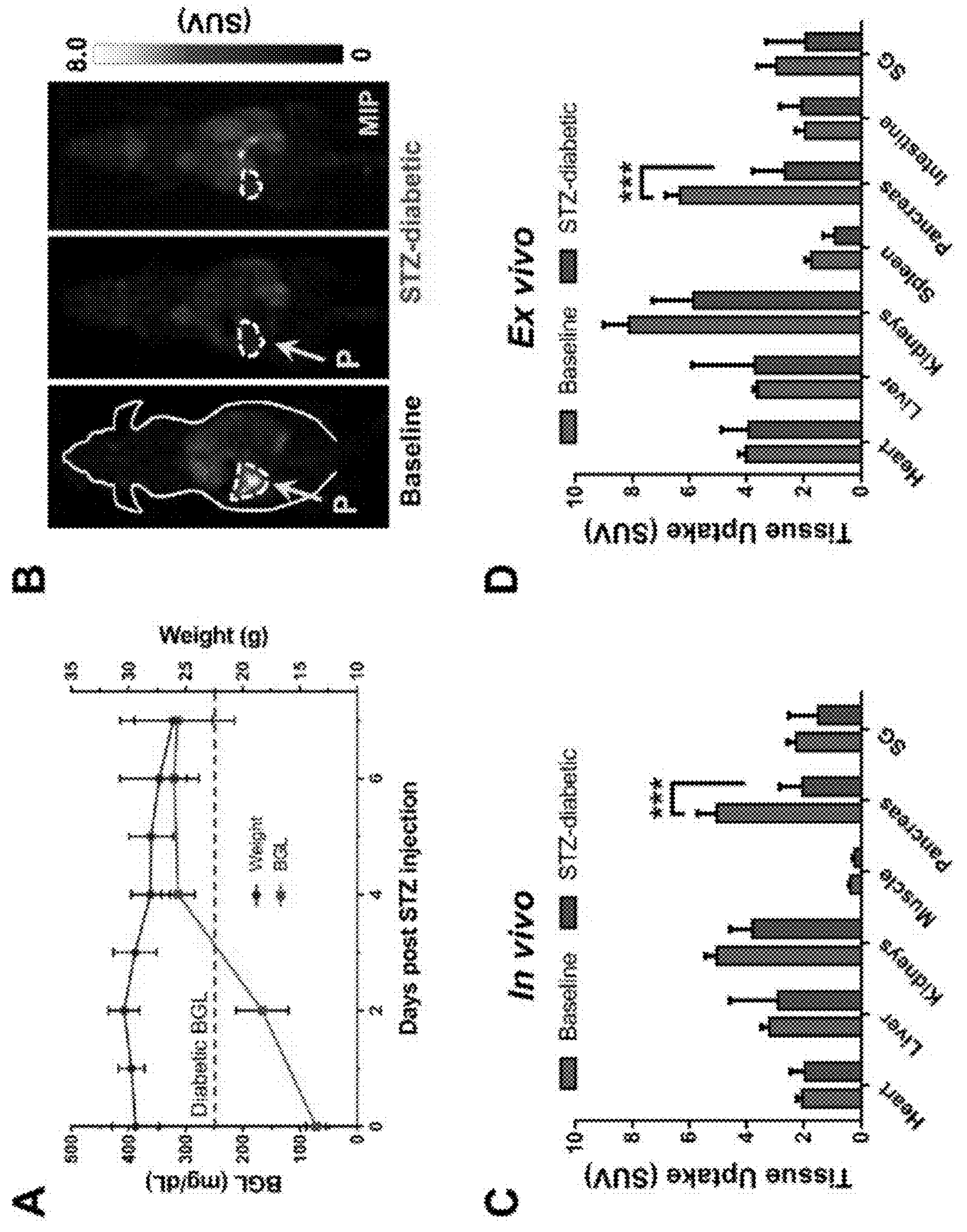
FIGS. 8A-8D show $^{52}Mn^{2+}$-PET imaging in a mouse model of type 1 diabetes.

The correlation between pancreatic $^{52}Mn^{2+}$ uptake and beta cell functional was investigated in a murine model of type-1 diabetes. Diabetes was induced in ICR female mice via injection of a single STZ (180 mg/kg) dose, a well-established and extensively studied model in the literature. As observed in FIG. 8A, four days after induction, mice presented signs of hyperglycemia (blood glucose >250 mg/dL) and weight loss that indicated a diabetic status. As seen in the PET images (FIG. 8B), $^{52}Mn^{2+}$ accretion within the pancreas of diabetic mice was significantly (P<0.0001) reduced from 5.13±0.38 SUV (n=3) in normal mice to 2.04±0.81 SUV (n=3) in diabetic mice (FIG. 8C). Ex vivo biodistribution corroborated a >58% decrease in pancreatic accumulation of $^{52}Mn^{2+}$ (FIG. 8D). These results further demonstrated the specificity and the potential of radiomanganese PET imaging to detect changes in beta cell mass noninvasively.

$^{52}Mn^{24}$ Uptake in Pre-Type 2 Diabetic Mice

Figures 9A, 9B:
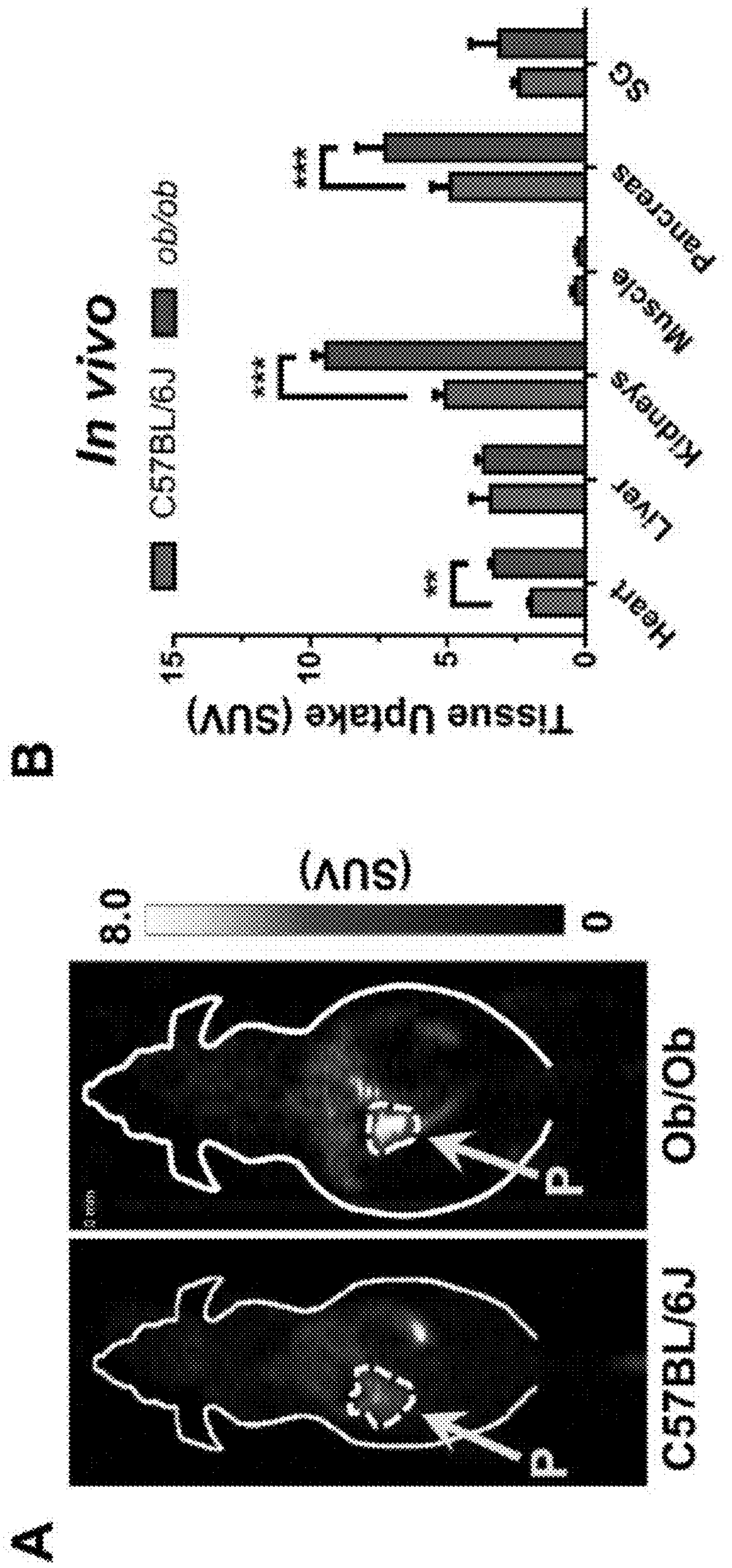
FIGS. 9A-9B show $^{52}Mn$-based PET imaging in pre-type 2 diabetic ob/ob mice.
Figures 10A, 10B, 10C, 10D:
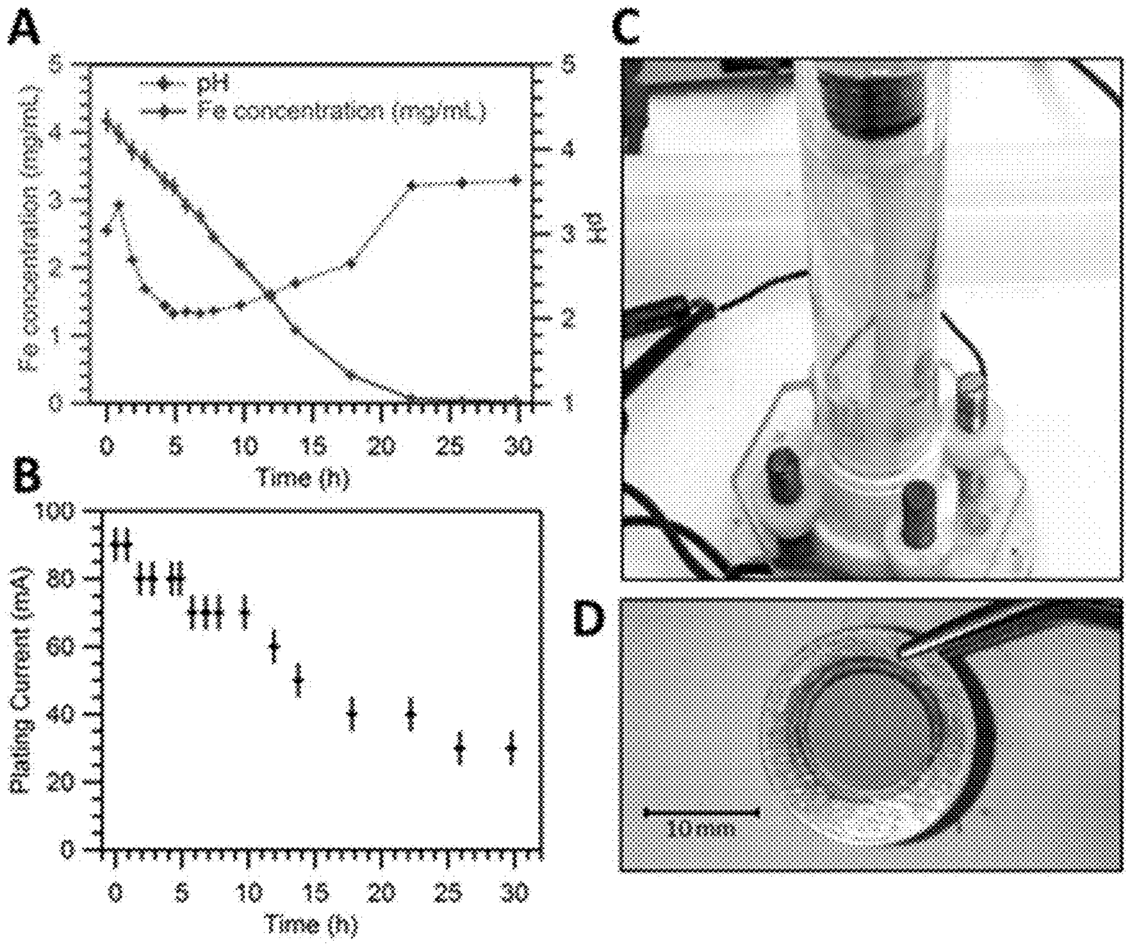
FIG. 10A shows concentration of iron in electrodeposition solution as a function of time (red) and solution pH as a function of time (blue). Iron concentration was measured by microwave plasma atomic emission spectroscopy (MP-AES).
FIG. 10B shows plating current as a function of time with plating potential held constant at 7.0±0.1 V.
FIG. 10C shows a plating cell at the start of plating. During plating the light green color becomes colorless.
FIG. 10D shows an electroplated Fe-54 target on silver disc substrate.

Imaging studies were also performed in C57BL/6J mice carrying the lepob (ob/ob) spontaneous mutation that result in animal obesity and pre-diabetic syndrome (i.e. pre-type 2 diabetes), which is another model that is well-established and extensively studied in the literature. Increased $^{52}Mn^{2+}$ accumulation in the pancreas of pre-type 2 diabetic ob/ob mice was observed in the PET data (FIG. 9A). Pancreatic uptake was 4.89±0.68 SUV in lean mice and 7.27±1.03 SUV in the pre-type 2 diabetic ob/ob mice (FIG. 9B), one hour after administration of $^{52}Mn^{2+}$ (n=3). Ex vivo biodistribution corroborated the statistically significant differences in pancreatic SUV between the groups (P<0.0001). Uptake in the liver and salivary gland was very similar in obese and lean animals with SUVs of 3.68±0.25 vs. 3.40±0.73 and 2.40±0.20 vs. 3.11±1.05, respectively.

DISCUSSION

The loss, dysfunction, or both, of pancreatic beta cells is a significant component of both type 1 and type 2 diabetes. The ability of beta cells to sequester divalent metal ions (e.g. $Ca^{2+}$, $Mn^{2+}$, $Zn^{2+}$, and $Co^{2+}$) is an important aspect of the production and release of insulin. While beta cell function has been widely investigated based on the measurement of $Ca^{2+}$ currents in vitro, little progress has been achieved in exploring beta cell divalent metal intake for measurement of function in vivo. Part of this is due to the lack of effective methods to track the distribution of most of these metals in vivo. Fortunately, $Mn^{2+}$ has both magnetic and nuclear properties that facilitate its noninvasive detection by both MRI and PET. In the example study discussed above, the use of radioactive manganese for noninvasive PET imaging of the mouse pancreas was investigated. When injected intravenously, $^{52}Mn^{2+}$ accumulated largely into pancreatic tissue with exceptionally fast blood extraction kinetics. $^{52}Mn^{2+}$ uptake in the pancreas, which peaked within minutes following administration in healthy mice, was on the order of 5-6 SUV with slow clearance half-life of approximately 8 days.

Two isotopes of manganese present themselves as excellent candidates for manganese-based PET: Mn-52 ($t_{1/2}$: 5.6 d, β+: 29.6%, $E\beta_{ave}$: 0.24 MeV) and Mn-51 ($t_{1/2}$: 45.6 min, β+: 97.1%, $E\beta_{ave}$: 0.96 MeV). Due to its high energy gamma emissions and relatively long half-life, Mn-52 is well-suited for preclinical small animal research. Mn-51, on the other hand, has excellent decay properties that are more amenable to clinical applications. With its longer half-life, Mn-52 can be shipped nationally or internationally, whereas Mn-51 must be produced and utilized on-site.

One of the more common production strategies for Mn-52 involves the low energy (Ep+<20 MeV) proton irradiation of $^{nat}Cr$ metal targets. In this example study, an ethanol/HCl-based anion exchange chromatography that allows for a Mn-52 recovery efficiency of greater than 60% in less than 2 hours was implemented. Overall, contamination including heavy metals such as $^{nat}Cr$ (<0.1 μg) was very low, making the isolated Mn-52 suitable for preclinical investigations.

The results of the example study described above revealed that the observed pancreatic radioactivity was a result of the specific uptake of $^{52}Mn^{2+}$ by pancreatic beta cells. By pharmacologically manipulating the mechanism of insulin secretion in isolated islets in vitro, the uptake of radioactive $^{52}Mn^{2+}$ could be correlated with $Ca^{2+}$ uptake. This agrees with other in vitro/ex vivo studies using non-radioactive $Mn^{2+}$ that reported a correlation between $Mn^{2+}$ uptake and beta cell functional capacity. Similarly, in vivo studies demonstrated that the chemical inhibition of insulin release, using nifedipine or diazoxide, resulted in a decline in the accumulation of $^{52}Mn^{2+}$ within the pancreas. In addition, the stimulation of insulin secretion with glibenclamide (5 mg/kg) led to an increase in $^{52}Mn^{2+}$ uptake in the pancreas. Overall, the results of this example study indicated that the $^{52}Mn^{2+}$ uptake observed in the pancreas was largely mediated by and dependent on the functional beta cell mass.

The example study also investigated whether PET imaging with radiomanganese was sensitive enough to detect changes in beta cell mass that occur during diabetes progression and disease. First, an experimental animal model of STZ-induced type-1 diabetes, which showed a ~60% reduction in the pancreatic accumulation of $^{52}Mn^{2+}$ while uptake in other organs remained unaltered, was employed. This indicates the ability of radiomanganese PET imaging for revealing extreme cases of beta cell loss. The gradual loss of beta cell mass under chronic exposure to low doses of STZ could be examined using Mn-51 ($t_{1/2}$=46 min) for longitudinal PET imaging.

In the obese mouse (ob/ob) model of pre-type 2 diabetes, significant (P<0.0001) enhancement in pancreatic uptake of $^{52}Mn^{2+}$ was observed. These results agree with previous reports showing that ob/ob mice do not progress to type 2 diabetes, but rather present markedly higher beta cell mass compared with lean mice at 10 weeks of age. An increased beta cell mass in this population is consistent with the increased pancreatic uptake of $^{52}Mn^{2+}$ that was observed in this example study, which demonstrates the potential of radiomanganese PET for noninvasively quantifying variations in beta cell mass within the context of type 2 diabetes, particularly at the early stage of disease progression.

Because there can be significant changes in beta cell function long before changes in beta cell mass are observed, it is advantageous that the relative uptake of radiomanganese in vivo depends on the functional beta cell mass. This ability has the potential to shed light on the survival of beta cell transplants, and on the rate of functional beta cell mass decline in asymptomatic type 1 diabetic patients.

The diffusion of $Mn^{2+}$ through beta cell VDCCs depends on functional activation by glucose or drug-based stimulation. This has been shown in this example study through in vitro and in vivo functional suppression and enhancement studies. For a given state of glucose activation, the amount of $Mn^{2+}$ cellular internalization is relative to the number of available VDCCs, which should be proportional to functional beta cell mass. Furthermore, accurate quantification of functional beta cell mass can include subtraction of nonspecific exocrine pancreas tracer uptake of the radiotracer. This may be accomplished through pharmacological manipulation to acutely suppress beta cell uptake using nifedipine, isoflurane, diazoxide, or other suppressing agents.

Our studies also provided valuable information on the kinetics of the whole-body distribution of $^{52}Mn^{2+}$. Besides specifically accreting in pancreatic islets, $^{52}Mn^{2+}$ also accumulated in the liver, heart, kidneys, and salivary gland. Despite the significant kidney uptake, no clear sign of renal excretion was observed and most of the $^{52}Mn^{2+}$ clearance occurred through the hepatobiliary system. From the analysis of the image-derived dynamic TAC of the heart, a $^{52}Mn^{2+}$ circulation half-life of 10.7±3.5 s following a rapid bolus injection was estimated, which aligned with previous studies showing an extremely fast (~0.8 min) blood clearance of Mn-54 in dogs. Such fast extraction kinetics and the lack of evidence of $^{52}Mn^{2+}$ metabolites in blood indicate that compartmental modeling could be used to describe $^{52}Mn^{2+}$ uptake in a more quantitative manner.

Several PET tracers have been studied as potential beta cell imaging agents. [$^{11}$C]-Dihydrotetrabenazine (DTBZ) and the $^{18}$F-labeled DTBZ analog FP-(+)-DTBZ have been shown to have high affinity for the type 2 vesicular acetylcholine transporter (VMAT2), which is expressed on the surface of rodent beta cells, but appears to be entirely absent from pancreatic exocrine tissue. Unfortunately, primate models have shown very low pancreatic uptake of [$^{11}$C]-DTBZ, which suggests that the degree of VMAT2 expression is species-dependent.

Another category of tracers includes radiolabeled (e.g. F-18, Ga-68, Cu-64, In-111) derivatives of exendin-4, a glucagon-like protein-1 receptor (GLP-1R) agonist. Fluorescence microscopy has shown that GLP-1R is only located on beta cells within the human pancreas, making it an attractive molecular imaging target due to its specificity. Unfortunately, exendin-4 also suffers from low pancreatic uptake (less than 0.3% ID/g in Sprague-Dawley rats at 1 h post injection whereas proximal kidney uptake was greater than ~25% ID/g). In general, the implementation of tracers targeting surface receptors of beta cells is challenging, considering the low total mass of beta cells, diffuse pancreatic distribution, and heterogeneous receptor expression.

Aside from following the decline in beta cell mass of type 1 diabetic patients, there is a pressing need for a noninvasive method for longitudinal imaging of pancreatic islet transplants. Islet transplantation has been shown to lead to insulin independence for several years in patients with type 1 diabetes, but has not been widely adopted due to the need for donor tissues. Recent advances in selective stem cell differentiation techniques will likely lead to wider clinical adoption of beta cell transplantation therapies. The ability to noninvasively track the survival and function of transplanted beta cells would enable research into the patient-specific efficacy of immune-modulating therapies and the development of new therapeutic strategies. The use of radiomanganese PET for monitoring islet transplant survival is compelling, since it can be performed repeatedly over time.

Example: Preparation and In Vivo Characterization of $^{52}MnCl_2$ for PET Imaging of $Ca^{2+}$ Transport In this example study, methods for the production of Mn-51 on low-energy medical cyclotrons were investigated. In general, Mn-51 was produced by proton irradiation of electrodeposited isotopically-enriched Fe-54 targets followed by anion exchange chromatography. Initial $^{51}MnCl_2$ pharmacokinetic characterization in mice and predicted human dosimetry showed promise for a variety of PET applications, including VDCC activation imaging in pancreatic beta cells.

Materials and Methods

Materials and Nomenclature

All reagents used in this example study were obtained from commercial vendors and were used as received unless otherwise stated. Aqueous solutions were constituted in >18 MΩ/cm $H_2O$. Tissue uptake of radioactivity is specified in standardized uptake values (SUV), defined as the product of the percentage of injected dose per gram of tissue (% ID/g*100) and the body weight (g) of the subject. Unless otherwise stated, all values are specified as mean±standard deviation.

Fe-54 Target Fabrication and Irradiation

Targets were prepared by electrolytic deposition of isotopically enriched Fe-54 metal (<100 mg) on Ag disc substrates (0.5 mm thick, 19 mm diameter). Briefly, Fe-54-enriched metal (99.93%, Isoflex USA, San Francisco, CA) was dissolved in 2-5 mL of 6 M HCl. To this solution, 100 μL of 30% $H_2O_2$ was added to promote the Fe(III) oxidation state. This solution was taken to near dryness (<1 mL), before adding 15 mL of saturated ammonium oxalate solution (stock solution stored with ~g Chelex® 100 resin to minimize trace metal impurities). Approximately 100 mg of L-ascorbic acid was added to this solution to promote the reduction of Fe(III) cations during electrodeposition. This solution was adjusted to pH~3.0 using 6 M NaOH or 6 M HCl and transferred to a cylindrical plating cell. A platinum wire anode was positioned approximately 1 cm above the silver disc substrate, and a potential of 7.0±0.1 V was applied corresponding to an initial current of 0.09±0.01 A (115±13 mA/cm$^2$). Electrical current and pH were measured at multiple time-points during electrodeposition. 20 μL aliquots of the plating solution were also collected at multiple time-points for Fe-concentration measurements by microwave plasma atomic emission spectroscopy (MP-AES, Agilent Technologies, Santa Clara, CA). When electrodeposition had completed as determined by the electrolyte becoming colorless (~24 hours), targets were dried and weighed to determine the plated Fe-54 mass.

Targets were irradiated by 16 MeV protons (PETtrace 800, GE Healthcare, Chicago, IL) with water-jet cooling on the rear target face. Beam currents of up to 60 μA were applied without changes in target appearance. Following irradiation, the short-lived Co-54 ($t_{1/2}$: 1.5 min) impurity was allowed to decay for 10 minutes before dismounting the target. Activities were quantified by efficiency-calibrated high-purity germanium (HPGe) gamma spectroscopy, and end of bombardment (EoB) decay correction was performed using the nominal Mn-51 half-life (45.6 min).

Mn(II)/Fe(III) Separation Chemistry

Following irradiation, targets were placed in a cylindrical dissolution cell, whereby an o-ring sealed against the front of the target face around the electrodeposited and irradiated Fe-54 material. After the addition of 2 mL of 11M HCl, the reaction vessel was brought to 80° C. Dissolution was found to be complete in less than 20 minutes. To this solution, 1.8 mL $H_2O$+0.2 mL 30% $H_2O_2$ was added before transferring to a 15 mL (1.5 cm diameter) AG-1×8 strongly-basic anion exchange column which had been equilibrated with ~5 column volumes of 5 M HCl. Using 5 M HCl as mobile phase, the first 5 mL of eluent were discarded. The following 10 mL, containing the Mn-51 product, were collected in a pear-shaped rotary evaporator flask. The Mn-51 product was taken to dryness under reduced atmosphere, and the resulting $^{51}MnCl_2$ residue was redissolved in ~500 μl of pH 6.5 0.01 M NaOAc buffer. The enriched Fe-54 target material was recovered from the separation column in 30-50 mL of 0.1 M HCl, which was subsequently taken to dryness (ferric chloride) by boiling under $N_2$ gas flow.

The Mn(II) oxidation state following separation was confirmed by thin-layer chromatographic techniques. Residual iron impurities in the final Mn-51 product were quantified by MP-AES analysis. An effective specific activity was measured by competitive DOTA chelation (room temperature, 0.15 M NaOAc, pH~6.0, 1 hour) followed by silica thin-layer chromatography (0.25 M $NH_4OH$). The mass of DOTA required to bind 50% of a sample's activity was interpolated from the resulting sigmoidal binding curve, and effective specific activity was calculated as the amount of activity divided by twice this mass.

Animal Model, PET/CT Imaging

All animal studies were conducted under a protocol approved by the University of Wisconsin Institutional Animal Care and Use Committee. Non-fasted healthy ICR mice (Envigo, Indianapolis, IN) were divided into two groups. Mice in the first group (n=2) were anaesthetized by isoflurane (4% induction, 1% maintenance), tail-vein catheters were affixed, and mice were placed on the microPET/CT bed in a prone position (Inveon, Siemens Preclinical Solutions, Knoxville, TN). Dynamic PET acquisition was started and $^{51}Mn^{2+}$ was administered in a rapid bolus (3.3 MBq, 200 μl, 10% 0.01 M NaOAc/90% PBS) through the tail-vein catheter. Sixty minutes of dynamic PET data were acquired following $^{51}Mn^{2+}$ administration. Due to the impact of volatile anesthetics on voltage-dependent calcium channel (VDCC) activation, the second group (n=3) received an intravenous (I.V.) bolus of $^{51}Mn^{2+}$ (1.6 MBq, 200 μL, 10% 0.01 M NaOAc/90% PBS) while awake. 60 minutes post-injection mice were anaesthetized by isoflurane and a 10 minute static PET scan acquired. Following imaging, mice were immediately sacrificed by $CO_2$ asphyxiation, and organs were extracted. Ex vivo biodistribution measurements were performed by gamma counting (Wizard 2480, PerkinElmer, Waltham, MA).

Dynamic PET data were binned into 46 frames (12×5 s, 6×10 s, 6×30 s, 6×150 s, 6×300 s) and frames were reconstructed using non-scatter-corrected 3D ordered-subset expectation maximization followed by maximum a posteriori reconstruction (OSEM3D/MAP). Static PET data were reconstructed into a single frame by OSEM3D/MAP.

Dosimetry Calculations

Due to the rapid blood clearance of $Mn^{2+}$, OLINDA (Organ Level INternal Dose Assessment) dosimetry calculations were performed assuming instant compartment localization with organ activity fractions equal to those measured by ex vivo biodistribution herein. Based on the previously measured lengthy organ residence times of $Mn^{2+}$, it was also assumed that the effective organ clearance half-life (Ter) was equal to the radioactive half-life of Mn-51 ($t_{1/2}$: 45.6 min). It was also assumed that Mn-51 injections were 100% radionuclidically pure. In regards to the daughter isotope, Cr-51 ($t_{1/2}$: 27.7 d), it was assumed that the activity remained in same organ compartments as the parent Mn-51 biodistribution without biological clearance. Standard radiation weighting factors were used (γ=1, β=1). Source-organ integrated decays for Mn-51 and Cr-51 are tabulated in Table 2. Based on these assumptions, effective dose (ED) and effective dose equivalent (EDE) (units of mSv/MBq) were calculated for a standard adult male and female.

TABLE 2

Source organ integrated disintigrations for Mn-51 and Cr-51 used in OLINDA dose calculations.

| Tissue | Number of $^{51}$Mn disintigrations (MBq-h/MBq) | Number of $^{51}$Cr disintigrations (MBq-h/MBq) |
|---|---|---|
| Adrenals | 0.00E+00 | 0.00E+00 |
| Brain | 4.43E−03 | 3.93E+00 |
| Breasts | 0.00E+00 | 0.00E+00 |
| Gallbladder Contents | 0.00E+00 | 0.00E+00 |
| LLI | 0.00E+00 | 0.00E+00 |
| Small Intestine | 0.00E+00 | 0.00E+00 |
| Stomach | 0.00E+00 | 1.23E+01 |
| ULI | 6.42E−03 | 5.70E+00 |
| Heart Contents | 0.00E+00 | 0.00E+00 |
| Heart Wall | 2.37E−02 | 2.10E+01 |
| Kidneys | 6.91E−02 | 6.12E+01 |
| Liver | 6.30E−02 | 5.58E+01 |
| Lungs | 1.68E−02 | 1.49E+01 |
| Muscle | 2.18E−03 | 1.93E+00 |
| Ovaries | 0.00E+00 | 0.00E+00 |
| Pancreas | 4.11E−02 | 3.64E+01 |
| Red Marrow | 0.00E+00 | 0.00E+00 |
| Cortical Bone | 8.40E−04 | 7.48E−01 |
| Trabecular Bone | 0.00E+00 | 0.00E+00 |
| Spleen | 9.16E−03 | 8.12E+00 |
| Testes | 0.00E+00 | 0.00E+00 |
| Thymus | 0.00E+00 | 0.00E+00 |
| Thyroid | 0.00E+00 | 0.00E+00 |
| Urinary Bladder Contents | 0.00E+00 | 0.00E+00 |
| Uterus/Uterine Wall | 0.00E+00 | 0.00E+00 |
| Total Body | 8.70E−01 | 7.20E+02 |

Results

Fe-54 Target Fabrication and Irradiation Results

Electrodeposition was found to be complete in approximately 24 hours with residual iron concentration dropping to <0.04 mg/mL (~0.5 mg Fe-54 unplated). Changes in plating metrics during electrodeposition are shown in FIGS. 10A-10D. The electroplated Fe-54 material appeared dark grey in color, rough in texture, and strongly adhered to the Ag substrate. Occasionally, slight oxidation could be seen near the periphery of the electroplated area, but this appeared to reduce during target irradiation. Precipitation was observed during pH adjustment in solutions containing greater than ~100 mg of iron. This may indicate that larger electrolyte volumes may be needed in order to produce high-mass targets. Targets were irradiated with up to 60 μA of 16 MeV protons, and no change in target appearance was observed. Targets of thicknesses 46.2-64.4 mg/cm$^2$ were irradiated by 30 μA of 16 MeV protons for one hour, and end of bombardment (EoB) yield was 1.21-1.66 GBq, as measured by efficiency-calibrated HPGe gamma spectroscopy.

Mn-51 Separation and Fe-54 Recovery

Total chemistry duration including dissolution, separation, dry-down, and final formulation was found to be approximately 90 minutes. Decay-corrected Mn-51 yield was 67.3±12.6% (n=3). Recovery yields could be improved by collecting more than 10 mL of eluent at the expense of increased separation and dry-down duration. For targets of thicknesses 46-64 mg/cm$^2$ (n=3) irradiated by 30 μA of 16 MeV protons for one hour, end of chemistry (EoC) yield was found to be ~185-370 MBq (n=3).

Final iron impurity masses for three production trials are listed in Table 3, along with corresponding separation factors.

TABLE 3

Mn-51 irradiation yields and separation results from three production trials.

| Trial # | Target Thickness (mg/cm$^2$) | EoB Yield (GBq) | Final Fe Impurity Mass (μg) | Separation factor |
|---|---|---|---|---|
| 1 | 64.4 | 1.66 ± 0.08 | 8.89 ± 0.08 | (3.92 ± 0.03) × $10^3$ |
| 2 | 58.1 | 1.31 ± 0.07 | 0.72 ± 0.01 | (3.42 ± 0.05) × $10^4$ |
| 3 | 46.2 | 1.21 ± 0.06 | 0.043 ± 0.001 | (6.67 ± 0.15) × $10^5$ |

Fe-54 recovery efficiency between productions was found to be 94.3±4.2% (n=3). The final Mn-51 product, decay-corrected to EoB, was found to be >99.9% radionuclidically pure by HPGe gamma spectroscopy with the Cr-51 daughter being the largest impurity (0.08%/). Trace radionuclidic impurities are listed in Table 4. An EoB effective specific activity of 7.4 GBq/μmol (1.9 GBq/μmol at EoC, n=1) was measured by titration with DOTA.

TABLE 4

Radionuclidic purity of separated Mn-51 product measured by HPGe gamma spectroscopy.

| Isotope | $t_{1/2}$ | EoB Activity Fraction | EoC Activity Fraction |
|---|---|---|---|
| $^{51}$Mn | 45.6 m | 99.91% | 99.34% |
| $^{52}$Mn | 5.59 d | 0.0001% | 0.0004% |
| $^{51}$Cr | 27.7 d | 0.08% | 0.61% |
| $^{55}$Co | 17.5 h | 0.012% | 0.045% |
| $^{56}$Co | 77.2 d | 0.0009% | 0.003% |
| $^{57}$Co | 272 d | 0.00002% | 0.00009% |

PET Results

Figure 11:
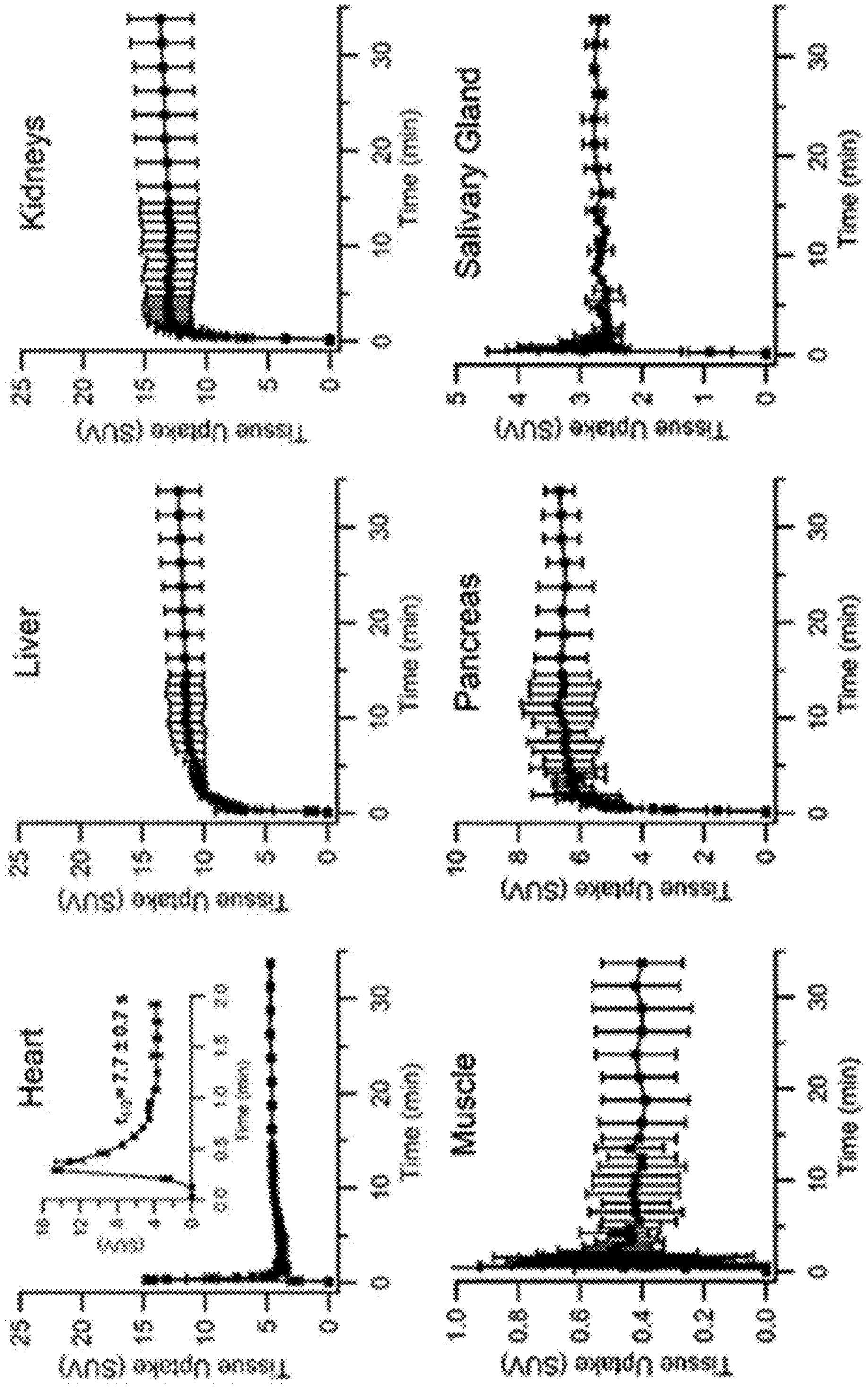
FIG. 11 shows dynamic PET time-activity curves (TACs) of organ ROIs in ICR mice (n=2, mean±SD) injected with a rapid intravenous bolus of $^{51}Mn(II)$, imaged for 30 minutes post-injection.

Rapid Mn-51 accumulation in the heart, liver, kidneys, pancreas, and salivary glands was observed in ICR mice (n=5) following a rapid intravenous bolus injection. PET time-activity curves (TACs) are shown in FIG. 11. Following initial distribution (<1 min), uptake was observed to be stable over 30 minutes of PET imaging, which is consistent with previous findings employing $^{52g}Mn^{2+}$. A heart blood-pool clearance half-life of 7.7±0.7 seconds was determined by weighted exponential least squares regression of the heart TAC from 0.375 to 3.25 minutes post-injection.

Figures 12A, 12B, 12C:
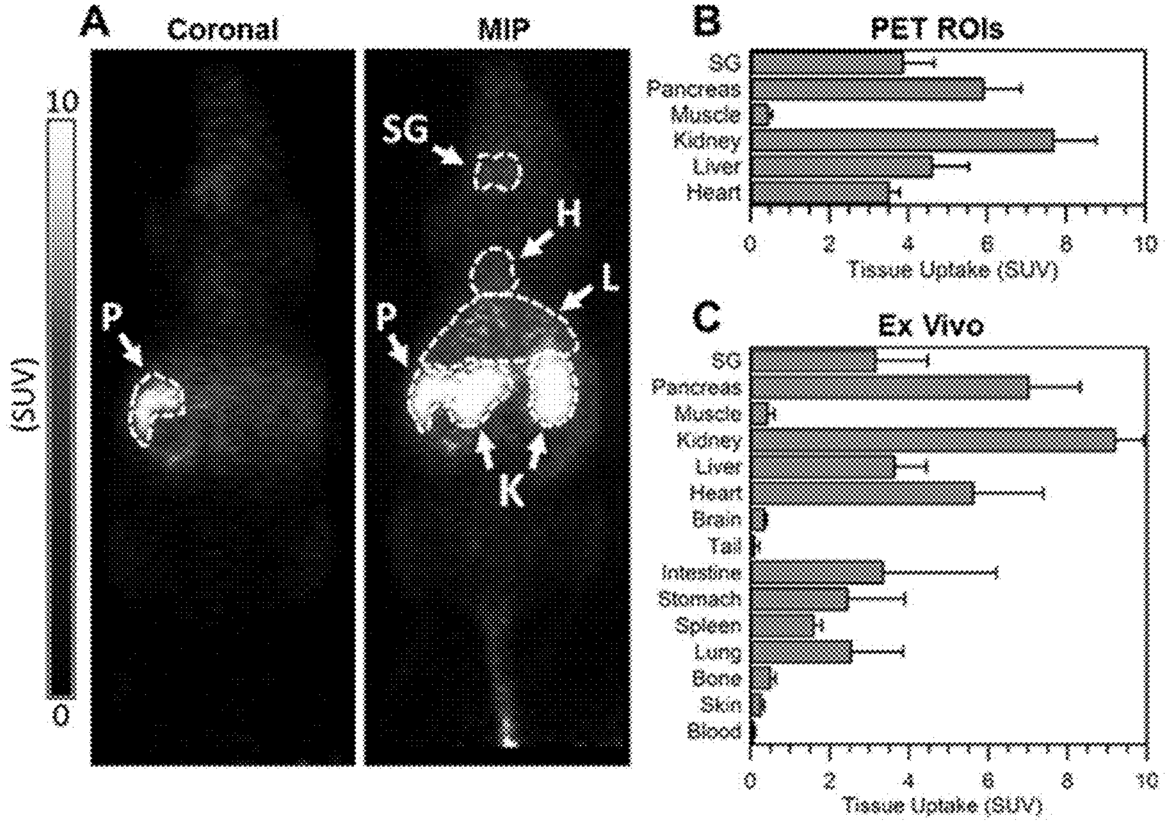
FIG. 12A shows coronal slice and maximum intensity projection (MIP) static PET images of a representative ICR mouse injected intravenously with $^{51}Mn(II)$ (non-anaesthetized during injection). PET images were acquired one hour post-injection. Pancreas (P), salivary gland (SG), heart (H), liver (L) and kidneys (K) indicated by arrows.
FIG. 12B shows $^{51}Mn$ tissue uptake quantification of hand-drawn PET ROIs in ICR mice (n=3, mean±SD) injected with a rapid intravenous bolus of $^{51}Mn(II)$.
FIG. 12C shows ex vivo $^{51}Mn$ biodistribution in ICR mice (n=3, mean±SD) immediately following PET imaging, measured by gamma counting.

Delineation of the pancreas from the surrounding organs (e.g., the kidneys) was readily achieved in static PET images (FIG. 12A). PET ROI quantification (FIG. 12B) and ex vivo biodistribution by gamma counting (FIG. 12C) show little activity in the muscle and blood, which is consistent with results from dynamic PET imaging. Ex vivo biodistribution showed highest Mn-51 uptake in the kidneys (9.2±0.7 SUV), followed by the pancreas (7.0±1.3 SUV) and the heart (5.6±1.8 SUV). Comparing dynamic PET subjects (n=2, I.V. $^{51}MnCl_2$ bolus under isoflurane) with static PET subjects (n=3, I.V. $^{51}MnCl_2$ non-anaesthetized) revealed significantly higher kidney uptake in anaesthetized dynamic PET subjects, 13.7±2.6 versus 7.7±1.1 (p=0.03).

Good agreement was observed between in vivo PET quantification and ex vivo gamma counting in all tissues with the exception of the heart. Because tissues are rinsed and wicked dry prior to weighing and gamma counting, this discrepancy in measured heart uptake is likely due to the inclusion of low-activity blood mass in heart PET ROIs. Intersubject biodistribution variability was found to be minimal when using the SUV uptake metric despite highly varied subject weights (37.6, 48.3, and 22.1 g). As expected, greater intersubject biodistribution variability was observed when using the % ID/g uptake metric.

Dosimetry Calculation Results

Mn-51 was found to have an EDE of 0.0362 mSv/MBq and 0.0422 mSv/MBq for the standard male and female human model respectively. The daughter isotope Cr-51 was found to have an EDE of 0.267 mSv/MBq and 0.324 mSv/MBq for the standard male and female model respectively. OLINDA dosimetry predictions for a typical clinical dose (370 MBq, 10 mCi) are listed in Table 5.

TABLE 5

Effective dose equivalent (EDE) for a 370 MBq intravenous injection of radionuclidically pure $^{51}Mn^{2+}$ in the standard adult human male and female.

| Contribution | Male (mSv) | Female (mSv) |
|---|---|---|
| $^{51}$Mn | 13.4 | 15.6 |
| $^{51}$Cr | 0.11 | 0.14 |
| Total | 13.5 | 15.8 |

DISCUSSION

Manganese is an essential trace element in mammalian biology and has many prospective applications as an imaging agent in medicine. Mn-51 is well suited for clinical PET based on its decay characteristics.

The electrodeposition method described in this example study was effective for the quantitative reduction of $^{54}$Fe(III) to Fe-54 metal, with the electroplated iron metal being strongly adhered to the silver disc substrate. From FIG. 10A, it can be inferred that $^{54}$Fe(III) reduction follows zero-order kinetics for the majority of the plating duration. This suggests that plating time may vary depending on the Fe-54 mass in solution. The plating solution pH was found to be highly variable during electrodeposition, with the solution rising above pH 3.0 upon completion. This acute rise in pH near plating completion may enable non-colorimetric automation methods.

The fabricated Fe-54 targets were robust, withstanding relatively high beam currents (16 MeV, 60 μA) without changes in appearance. The target thicknesses (~45-65 mg/cm$^2$) and irradiation parameters (30 μA for 1 h) used in this example study were sufficient to provide enough EoC activity (~185-370 MBq) for several small animal studies or approximately one human study. EoC yield could readily be increased to 1.5-2.0 GBq by employing target thicknesses of approximately 100 mg/cm$^2$ and irradiating with a beam current of 60 μA for two hours. Based on these yields, a chemistry duration of ~90 minutes is sufficiently short for production purposes. However at institutions without solidtarget capabilities, a solution-target of $^{54}Fe(NO_3)_2$ or $^{50}Cr(NO_3)_3$ could provide elegant alternative production routes. Although the chemical isolation of Mn-51 from bulk iron metal is simpler than Mn-51 from bulk chromium, the production cross section for $^{50}Cr(d,n)$ is significantly higher than $^{54}Fe(p,\alpha)$ which may help compensate for the reduced target atomic fraction in solution targets.

PET imaging of pancreatic beta cells with $^{51}MnCl_2$ appears promising due to the rapid blood clearance and significant pancreatic accumulation. Further studies are needed to determine the feasibility and optimal study methodology for functional beta cell mass quantification by $^{51}$Mn-PET. To this end, it is contemplated that non-specific exocrine uptake can be quantified by co-injection of VDCC blocking agents, such as nifedipine. Other positron-emitting divalent metals such as $^{63}Zn^{2+}$ ($t_{1/2}$: 38.5 min β+: 92.7%, $E\beta_{ave}$: 0.92 MeV) may also prove useful for beta cell related investigations, as VDCCs are permeable to $Zn^{2+}$ and significant $^{63}Zn^{2+}$ pancreatic uptake has been observed in mice in other studies.

The heart blood-pool clearance half-life of $^{51}Mn^{2+}$ found in this example study (7.7±0.7 s) was rapid, suggesting first-pass tissue localization kinetics. Rapid blood clearance and stable accumulation offers experimental flexibility with regards to PET imaging duration and timing following tracer administration. Tracer kinetics such as these also support the use of the SUV uptake metric for $^{51}$Mn-PET studies, as tracers without significant tissue clearance (e.g., [$^{18}$F]-FDG) lend themselves well to such analytic methods. Furthermore, the rapid blood clearance of $^{51}Mn^{2+}$ may enable multiple-injection protocols within a single patient study. Techniques such as these may prove useful in beta cell mass (BCM) quantification studies for the subtraction of non-specific exocrine pancreas uptake by stimulation or blocking (e.g., through glibendamide or nifedipine) of beta cell VDCCs following baseline imaging. On the other hand, the pulsatile nature of calcium transport may increase test-retest variability for bolus injection techniques. This effect could possibly be mitigated by administering $^{51}MnCl_2$ as an intravenous infusion over 5-15 minutes.

The mean positron energy emitted during the decay of Mn-51 (962 keV) is significantly higher than that of F-18 (250 keV) or $^{52g}$Mn (242 keV), which may lead to poorer spatial resolution in PET images. Regardless, the resolution of Mn-51 has still proven to be sufficient for whole-organ-ROI microPET studies, and positron range is not typically the limiting factor of clinical PET resolution.

Mn-51 dosimetry appears favorable, even when accounting for the long-lived daughter Cr-51, and making the conservative assumption that this daughter is not biologically excreted. In this example study, a cumulative effective dose equivalent of ~15 mSv for a 370 MBq Mn-51 PET study was calculated. This result was comparable to the average dose for an [$^{18}$F]-FDG study of 14.1 mSv. This suggests that it would be possible to perform up to three repeat PET studies in healthy or type-I diabetic volunteers without exceeding the annual non-stochastic International Commission on Radiological Protection (ICRP) limit of 50 mSv for research subjects.

The present disclosure has described one or more preferred embodiments, and it should be appreciated that many equivalents, alternatives, variations, and modifications, aside from those expressly stated, are possible and within the scope of the invention.

The invention claimed is:

1. A method for quantitatively imaging pancreatic beta cells using positron emission tomography (PET), the steps of the method comprising:

(a) administering radiomanganese to a subject;

(b) acquiring data from a region-of-interest containing a pancreas of the subject using a PET system;

(c) reconstructing an image of the region-of-interest from the acquired data, wherein the reconstructed image depicts a preferential uptake of free isotopes of the radiomanganese in pancreatic beta cells in the subject via voltage dependent $Ca^{2+}$ channels (VDCCs); and (d) processing the image with a computer system to estimate a quantitative parameter of pancreatic beta cell function based on a measured activity of the free isotopes of the radiomanganese taken up in the pancreatic beta cells in the subject via VDCCs, wherein the pancreatic beta cell function indicates insulin secretion of the pancreatic beta cells in the subject.

2. The method as recited in claim 1, wherein the radiomanganese comprises at least one of free radioisotopes of manganese or compounds that dissociate to produce free manganese when administered to the subject.

3. The method as recited in claim 2, wherein the radioisotopes of manganese include one of Mn-51 or Mn-52g.

4. The method as recited in claim 2, wherein the radiomanganese is administered to the subject in a dose having less than one micromolar of radiomanganese.

5. The method as recited in claim 1, wherein the radiomanganese is administered to the subject using a continuous infusion in which the radiomanganese is continuously infused into the subject over a duration of time.

6. The method as recited in claim 1, wherein the radiomanganese is administered to the subject in a single bolus.

7. The method as recited in claim 1, further comprising administering a pharmacological agent to the subject before administering the radiomanganese to the subject, wherein the pharmacological agent modulates pancreatic beta cell uptake of divalent metals.

8. The method as recited in claim 7, wherein the pharmacological agent modulates pancreatic beta cell uptake of $Ca^{2+}$.

9. The method as recited in claim 7, wherein the pharmacological agent inhibits uptake of divalent metals by the pancreatic beta cells.

10. The method as recited in claim 9, wherein the pharmacological agent includes one of nifedipine or diazoxide.

11. The method as recited in claim 9, further comprising estimating a quantitative parameter of beta cell mass based on a measured activity of the free isotopes of the radiomanganese taken up in the pancreatic beta cells in the subject via the VDCCs, wherein the image reconstructed in step (c) comprises a first image, and step (d) includes providing a second image that depicts an uptake of radiomanganese in pancreatic beta cells in the region-of-interest without modulation by the pharmacological agent, and wherein a difference image is generated by computing a difference between the first image and the second image, wherein the difference image indicates an estimate of quantitative pancreatic beta cell mass as a result of computing the difference between the first image and the second image in order to reduce non-specific exocrine pancreas tracer uptake in the second image.

12. The method as recited in claim 7, wherein the pharmacological agent stimulates uptake of divalent metals by the pancreatic beta cells.

13. The method as recited in claim 12, wherein the pharmacological agent includes one of D-glucose, glibenclamide, or tolbutamide.

14. The method as recited in claim 7, wherein step (d) includes correlating a modulated uptake of divalent metals by the pancreatic beta cells with an activity of radiomanganese in the reconstructed image to estimate a quantitative parameter of pancreatic beta cell function.

15. A method for imaging pancreatic beta cells using positron emission tomography (PET), the steps of the method comprising:

(a) providing to a computer system, a first image of a subject acquired with a PET system following a first administration of radiomanganese to the subject at a first time, wherein the first image depicts a first radiomanganese activity in the subject based on a first uptake of free isotopes of the radiomanganese in the subject's pancreas via voltage dependent $Ca^{2+}$ channels (VDCCs);

(b) providing to the computer system, a second image of the subject acquired with the PET system following a second administration of radiomanganese to the subject at a second time that is different from the first time, wherein the second image depicts a second radiomanganese activity in the subject based on a second uptake of free isotopes of the radiomanganese in the subject's pancreas via VDCCs;

(c) computing a difference between the first activity and the second activity; and (d) quantifying a pancreatic beta cell mass based on the computed difference, wherein the quantified beta cell mass is indicative of a change in beta cell mass as a function of time.

16. The method as recited in claim 15, wherein the radiomanganese includes one of Mn-51 or Mn-52g.

17. The method as recited in claim 15, wherein the first image is acquired with the PET system following administration of pharmacological agent that modulates pancreatic beta cell uptake of divalent metals before the administration of the radiomanganese.

18. The method as recited in claim 17, wherein the pharmacological agent modulates pancreatic beta cell uptake of $Ca^{2+}$.

19. The method as recited in claim 18, wherein the pharmacological agent stimulates uptake of divalent metals by the pancreatic beta cells.

20. The method as recited in claim 19, wherein the pharmacological agent includes one of D-glucose, glibenclamide, or tolbutamide.

21. The method as recited in claim 17, wherein the pharmacological agent inhibits uptake of divalent metals by the pancreatic beta cells.

22. The method as recited in claim 21, wherein the pharmacological agent includes one of nifedipine or diazoxide.

23. The method as recited in claim 15, wherein step (d) includes quantifying a functional pancreatic beta cell mass.

24. A method for assessing a pancreatic tissue transplant using positron emission tomography (PET), the steps of the method comprising:

(a) administering radiomanganese to a subject who has received a pancreatic tissue transplant;

(b) acquiring an image from a region-of-interest containing a pancreas of the subject with a PET system, wherein the image depicts an uptake of free isotopes of the radiomanganese in the subject's pancreas via voltage dependent $Ca^{2+}$ channels (VDCCs);

(c) computing a pancreatic beta cell mass from the acquired image based on a measured activity of the free isotopes of the radiomanganese taken up in the pancreatic beta cells in the subject via VDCCs;

(d) generating a report based on the computed pancreatic beta cell mass that contains information associated with an assessment of transplant viability of the pancreatic tissue transplant.

25. The method as recited in claim 24, wherein the pancreatic tissue transplant comprises a stem cell-based transplant.

* * * * *